(12) United States Patent
Beaulieu et al.

(10) Patent No.: US 8,349,566 B2
(45) Date of Patent: *Jan. 8, 2013

(54) METHODS FOR HIGH LEVEL MULTIPLEXED POLYMERASE CHAIN REACTIONS AND HOMOGENOUS MASS EXTENSION REACTIONS

(75) Inventors: Martin Beaulieu, San Diego, CA (US); Dirk Johannes Van Den Boom, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/193,390

(22) Filed: Jul. 28, 2011

(65) Prior Publication Data

US 2012/0015826 A1  Jan. 19, 2012

Related U.S. Application Data

(63) Continuation of application No. 10/903,268, filed on Jul. 30, 2004, now Pat. No. 8,003,317.

(60) Provisional application No. 60/492,102, filed on Jul. 31, 2003.

(51) Int. Cl.
*C12Q 1/68* (2006.01)
*C12P 19/34* (2006.01)
*C07H 21/04* (2006.01)

(52) U.S. Cl. .................... 435/6.12; 435/91.2; 536/24.33

(58) Field of Classification Search .......................... None
See application file for complete search history.

(56) References Cited

U.S. PATENT DOCUMENTS

| | | | |
|---|---|---|---|
| 4,988,617 A | | 1/1991 | Landegren et al. |
| 5,503,980 A | | 4/1996 | Cantor |
| 5,525,464 A | | 6/1996 | Drmanac et al. |
| 5,547,835 A | | 8/1996 | Koster |
| 5,622,824 A | | 4/1997 | Koster |
| 6,004,744 A | | 12/1999 | Goelet et al. |
| 6,015,664 A | * | 1/2000 | Henrickson et al. ............. 435/5 |
| 6,090,558 A | | 7/2000 | Monforte et al. |
| 7,014,994 B1 | | 3/2006 | Barany et al. |
| 7,364,897 B2 | * | 4/2008 | Heaney et al. ............. 435/287.2 |
| 8,003,317 B2 | * | 8/2011 | Beaulieu et al. ............. 435/6.12 |
| 2002/0040130 A1 | | 4/2002 | Braun |
| 2003/0027169 A1 | | 2/2003 | Zhang et al. |
| 2003/0232420 A1 | | 12/2003 | Braun et al. |
| 2005/0079521 A1 | | 4/2005 | Beaulieu et al. |

FOREIGN PATENT DOCUMENTS

| | | |
|---|---|---|
| WO | WO 01/27857 | 4/2001 |
| WO | WO 02/04489 | 1/2002 |
| WO | WO 2004/081576 | 9/2004 |

OTHER PUBLICATIONS

Aebersold and Mann, Nature 422:198-207 (2003).
Antos et al., Cire. Res., 89:997-1004 (2001).
Casey et al., J. Clin. Invest. 106:R31-38 (2000).
Cong, M. et al., J. Biol. Chem., 276(18):15192-15199.
Crawford et al. (2002) Biochemical and Biophysical Research Communications 293: pp. 509-516.
Ding and Cantor, PNAS, 1 00(6}:3059-3064 (2003).
Edwards and Gibbs., PCR methods and Applications, 3(4):365-375 (1994).
Fei and Smith., Rapid Comm. Mass. Spec., 14(11):950-959 (2000).
Harris and Limm, Cell Sci., 114:3219-3231 (2001).
Henegariu et al. (1997) Bio techniques 23 (3): 504-511.
Hsu et al. (2001) Biotechniques 31: pp. 560-570.
Kammer, S. et al., Proc. Natl. Acad. Sci., USA, 100(7):4066-4071 (2003).
Kirschner et al., Nat. Genet., 26:89-92 (2000).
Mahoney et al. (1997) Molecular Diagnosis vol. 2 (3): pp. 161-168.
Marx et al., Science 295:496-499 (2002).
McCabe et al., Biochem Med. And Metabolic Bio., 44(3):294-295 (1990).
Okamoto et al. (1999) Virology 259, pp. 428-436.
Reinitz et al., Arch. Biochem. Biophys., 348:391-402 (1997).
Robinson et al., Arch. Biochem. Biophys., 330:181-187 (1996).
Ross et al. (1998) Nature Biotechnol. vol. 16: pp. 1347-1351.
Sauer and Gut (2002) J. of Chromatography B vol. 782: pp. 73-87.
Shih, M. et al., J. Biol. Chem., 274(3):1588-1595 (1999).
Snapir, A. et al., Clin.Sci., 104:509-520 (2003).
Tang et al., Int J. Mass Spec., 226(1):37-54 (2003).
Thermosequenase Cycle kit (1999) Product No. US78500 sold by USB corporation.
Xu et al., J. Clin. Microbiol., 38(11 ):4114-4120 2000.
Yates, J. Mass Spec. 33:1-19 1998.
Zangenberg et al., PCR Applications: Protocols for Functional Genomics. Innis et al Eds. p. 73-94 (1999). Academic Press.

* cited by examiner

*Primary Examiner* — Prabha Chunduru
(74) *Attorney, Agent, or Firm* — Grant Anderson LLP

(57) ABSTRACT

Provided herein are optimized methods for performing multiplexed detection of a plurality of sequence variations. Also provided are methods for performing multiplexed amplification of target nucleic acid.

21 Claims, 1 Drawing Sheet

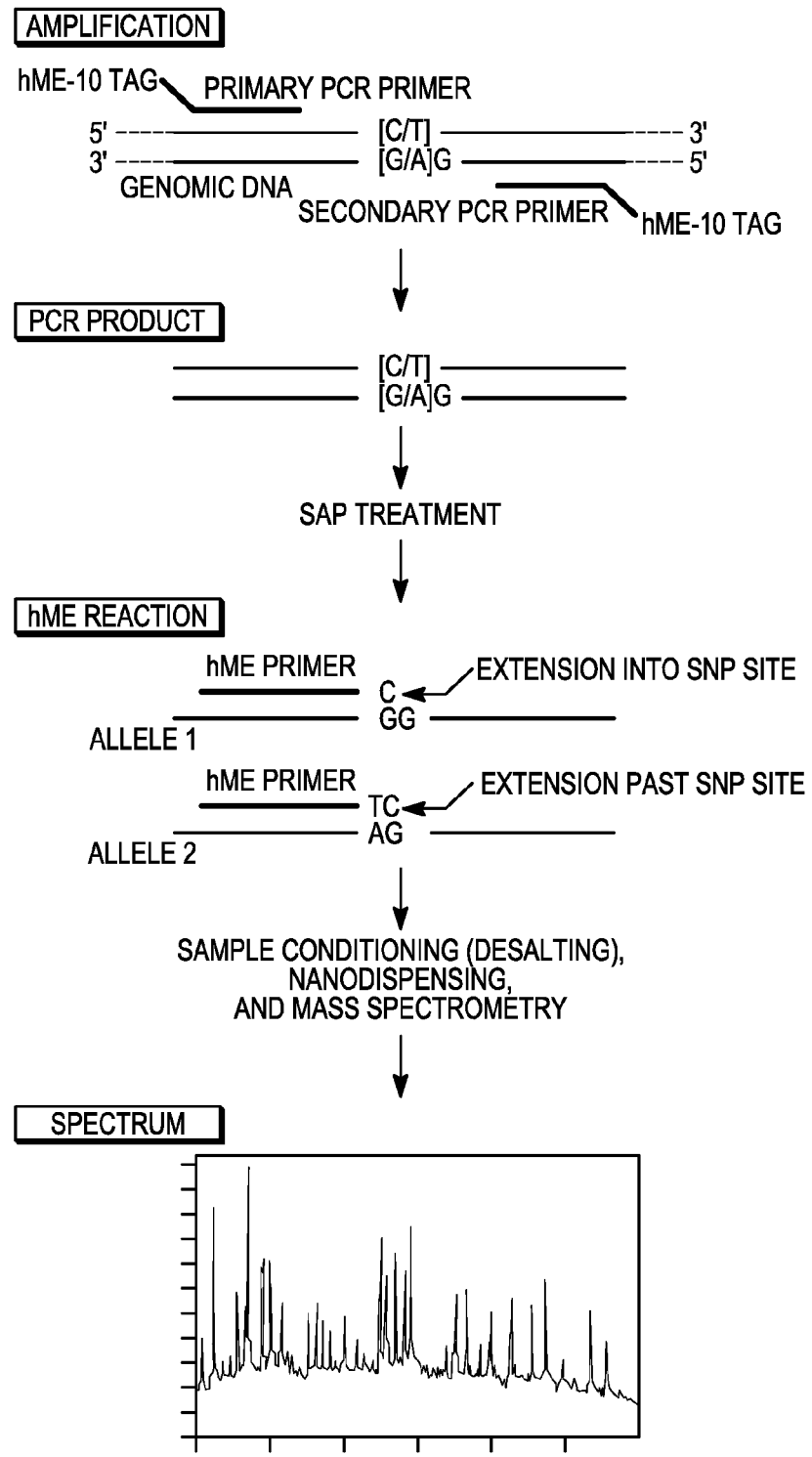

SEQUENCE LISTING

<160> NUMBER OF SEQ ID NOS: 37

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 1
acgttggatg aagaccacca ccctctccat g                                    31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
acgttggatg gctgagatgg tgttaaaggg                                      30

<210> SEQ ID NO 3
<211> LENGTH: 17
<212> TYPE: DNA
<213> ORGANISM: Artificial Sequence

```
<220> FEATURE:
<223> OTHER INFORMATION: Description of Artificial Sequence: Primer

<400> SEQUENCE: 3
ctcacgcccc tgccacc                                                          17

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
acgttggatg aatcacatgg catcaacacc                                            30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
acgttggatg tacagtaacc tagattaggc                                            30

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 6
gcatcaacac ccgccgc                                                          17

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 7
acgttggatg actgctgaag cagccacgac                                            30

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
acttggatga gcctcttgcc tacagtgtc                                             29

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 9
ccagggcagg ctcttct                                                          17
```

```
<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
acgttggatg tggtatcttc ggaagacacg                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
acgttggatg acaatgttgg atgcaaacgg                                    30

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 12
gttttgacag tgatgca                                                  17

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
acgttggatg gaaaggtcaa atacagcctc                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
acgttggatg cagctttcag ctggaggaac                                    30

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
aatacagcct cttgcttc                                                 18

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 16
acgttggatg tgaaatggct cagcctgtag                                                30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 17
acgttggatg ccctccattt ctgaggcagg                                                30

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 18
ctggtgtgcc acccagggc                                                            19

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
acgttggatg acacagatga tgaccagcag                                                30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
acgttggatg ttcctctcca gtccctcctg                                                30

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 21
agatggcagg gcccagagc                                                            19

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22
acgttggatg catttggcgg catgctgaag                                                30

```
<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 23
acgttggatg ccttcaaaag taccaaggcc                                    30

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
ctaggaagag ctagaggcaa                                               20

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 25
acgttggatg tggctgctcc ctgatcctaa                                    30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 26
acgttggatg catagccatc ttggataccc                                    30

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 27
ctccctgatc ctaacttctg a                                             21

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 28
acgttggatg tagaatgcta caaccaccgg                                    30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Primer
```

```
<400> SEQUENCE: 29
acgttggatg gtccctaatt caaaggtccc                                    30

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 30
tttgtcatta attggcctac a                                             21

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 31
acgttggatg gaattcttag atccagccac                                    30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 32
acgttggatg atggtcacag catacagctc                                    30

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 33
agtcaatgtt ttttgacaca agt                                           23

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 34
acgttggatg actgacagag attccttggc                                    30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 35
acgttggatg acatttctag agaaacaggc                                    30
```

```
<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 36
ttattayatc ttacacccaa atga                                          24

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
acgttggatg                                                          10
```

METHODS FOR HIGH LEVEL MULTIPLEXED POLYMERASE CHAIN REACTIONS AND HOMOGENOUS MASS EXTENSION REACTIONS

RELATED APPLICATIONS

This patent application is a continuation of U.S. patent application Ser. No. 10/903,268, filed Jul. 30, 2004, naming Martin Beaulieu and Dirk Johannes van den Boom as inventors, entitled METHODS FOR HIGH LEVEL MULTIPLEXED POLYMERASE CHAN REACTIONS AND HOMOGENOUS MASS EXTENSION REACTIONS, of which benefit of priority under 35 U.S.C. §119(e) is claimed to U.S. provisional application Ser. No. 60/492,102, filed Jul. 31, 2003, to Martin Beaulieu and Dirk van den Boom, entitled "METHODS FOR HIGH LEVEL MULTIPLEXED POLYMERASE CHAIN REACTIONS AND HOMOGENEOUS MASS EXTENSION REACTIONS,". This application is related to International PCT application No. PCT/US04/24953, filed the same day herewith, entitled "METHODS FOR HIGH LEVEL MULTIPLEXED POLYMERASE CHAIN REACTIONS AND HOMOGENEOUS MASS EXTENSION REACTIONS," to Sequenom, Inc., Martin Beaulieu and Dirk van den Boom. The subject matter of each of these applications is incorporated in its entirety by reference thereto.

FIELD OF THE INVENTION

Methods for biomolecular analysis are provided.

BACKGROUND OF THE INVENTION

Multiplex polymerase chain reaction (PCR) is a variant of PCR in which two or more target sequences can be amplified by including more than one pair of primers in the same reaction. Multiplex PCR has the potential to produce considerable savings of time and effort in the laboratory. Hurdles to achieving optimal multiplex PCR include poor sensitivity and specificity, low overall yield of amplified targets and/or preferential amplification of certain specific targets. The presence of more than one primer pair in the multiplex PCR increases the chance of obtaining spurious amplification products, primarily because of the formation of primer dimers. Preferential amplification of one target sequence over another is a known phenomenon in multiplex PCRs.

The homogenous primer mass extension (hME) assay is a reliable and reproducible method for the analysis of Single Nucleotide Polymorphisms (SNPs). The method employs mass spectrometry detection methods (see, e.g., Storm et al. (2003) *Methods Mol. Biol.* 212:241-262; and Tang et al. (2002) *Int. J. Mass. Spec.* 226:37-54; and FIG. 1). The speed and accuracy of matrix-assisted desorption ionization time-of-flight mass spectrometry (MALDI-TOF-MS) offers a solution for high-throughput genotyping. The hME assay is based upon annealing of an oligonucleotide primer adjacent to the SNP of interest. The addition of a DNA polymerase along with a preselected mixture of terminator nucleotides (e.g., ddNTPs) and non-terminator nucleotides (dNTPs), allows extension of the primer up to, or through, the polymorphic site, which generates uniquely detectable mass products. The resultant mass of the primer mass extension product is then analyzed by MALDI-TOF-MS and a genotype is assigned. Low level multiplex PCR amplification and primer extension reactions in a single reaction vessel have been described. There is a need for improved methods of performing higher level multiplex PCR amplification and multiplex primer mass extension reactions in a single well and to further increase the throughput and reduce the cost per genotype for primer mass extension reactions.

SUMMARY

Provided herein are optimized methods for performing a homogeneous primer mass extension (hME) assay, including an optimized PCR amplification reaction that produces amplified targets for subsequent multiplexed primer mass extension genotyping analysis using mass spectrometry. Also provided herein are optimized methods for performing multiplexed amplification reactions and multiplexed primer mass extension reactions (e.g., multiplexed hME assays) in a single well to further increase the throughput and reduce the cost per genotype for primer mass extension reactions. The nucleic acid target-region amplification and primer mass extension genotyping reactions have been optimized herein to permit moderate to high level multiplexing reactions with greater efficiency and accuracy, while at the same time not adversely affecting the mass spectrometry analysis of mass extension products.

For example, particular of $MgCl_2$ concentrations have been identified herein that permit high levels (e.g., 7-plex up to 50-plex or more) of multiplexed PCR and primer mass extension reactions along with successful mass spectrometry analysis. A consideration when selecting the concentrations of the dNTPs and $MgCl_2$ to use in the PCR amplification reaction that will be followed by a mass extension reaction and subsequent mass spectrometry analysis, is that the free $Mg^{2+}$ concentration of the PCR reaction mixture should be kept within a particular range that is high enough to permit robust PCR amplification, while being low enough to not adversely affect the subsequent mass extension reaction and mass spectrometry analysis.

Accordingly, provided herein are multiplex methods of genotyping a plurality of polymorphic loci, by simultaneously amplifying a plurality of nucleic acid-target regions under amplification conditions whereby at least 60% of 7 or more nucleic acid target-regions attempted are amplified by 7 or more primer pairs to produce an amplified mixture of nucleic acid-target regions containing polymorphic loci, contacting the amplified mixture of nucleic acid-target regions with 7 or more genotyping primers in the presence of at least one chain terminating reagent under primer mass extension conditions whereby the primers are extended up to, or through, the respective polymorphic loci, wherein there is one genotyping primer for each polymorphic locus within a nucleic acid-target molecule, and determining the mass of the extended genotyping primers, wherein at least 60% of the genotypes for said 7 or more nucleic acid target-regions attempted are determined. Further provided herein are multiplex methods of genotyping a plurality of polymorphic loci, by simultaneously amplifying a plurality of nucleic acid-target regions under amplification conditions whereby at least 60% of more nucleic acid target-regions attempted are amplified by 8 or more primer pairs to produce an amplified mixture of nucleic acid-target regions containing polymorphic loci, contacting the amplified mixture of nucleic acid-target regions with 8 or more genotyping primers in the presence of at least one chain terminating reagent under primer mass extension conditions whereby the primers are extended up to, or through, the respective polymorphic loci, wherein there is one genotyping primer for each polymorphic locus within a nucleic acid-target molecule, and determining the mass of the extended genotyping primers, wherein at least 60% of the genotypes for said 8 or more nucleic acid target-regions attempted are determined.

For example, provided herein are multiplex methods of genotyping a plurality of polymorphic loci, by simultaneously amplifying a plurality of nucleic acid-target regions under amplification conditions whereby at least 60% of 7 or more nucleic acid target-regions attempted are amplified by 7 or more primer pairs to produce an amplified mixture of nucleic acid-target regions containing a polymorphic loci; contacting the amplified mixture of nucleic acid-target regions with 7 or more genotyping primers in the presence of at least one deoxynucleotide and at least one chain terminating reagent under primer mass extension conditions whereby the primers are extended up to, or through, the respective polymorphic loci, wherein there is one genotyping primer for each polymorphic loci within a nucleic acid-target molecule; and determining the mass of the extended genotyping primers, wherein at least 60% of the genotypes for said 7 or more nucleic acid target-regions attempted are determined (i.e., are called). In other embodiments, the quantity of primer pairs can be selected from 8 or more, 9 or more, 10 or more, 11 or more, 12 or more, or 13 or more.

Also provided are multiplex methods of genotyping a plurality of polymorphic loci, comprising: simultaneously amplifying a plurality of nucleic acid-target regions under amplification conditions whereby at least 60% of 7 or more nucleic acid target-regions attempted are amplified by 7 or more primer pairs to produce an amplified mixture of nucleic acid-target regions, each containing a polymorphic loci, wherein only a single primer pair is used to amplify each particular nucleic acid target-region; contacting the amplified mixture of nucleic acid-target regions with 7 or more genotyping primers in the presence of four different "chain terminating reagents" under primer mass extension conditions whereby the primers are extended up to the respective polymorphic loci, wherein there is one genotyping primer for each polymorphic loci within a nucleic acid-target molecule; and determining the mass of the extended genotyping primers, wherein at least 60% of the genotypes for said 7 or more nucleic acid target-regions attempted are determined. In other embodiments, the quantity of primer pairs can be selected from 8 or more, 9 or more, 10 or more, 11 or more, 12 or more, or 13 or more.

Also provided are multiplex methods of genotyping a plurality of polymorphic loci, comprising: simultaneously amplifying a plurality of nucleic acid-target regions under amplification conditions whereby at least 60% of 13 or more nucleic acid target-regions attempted are amplified by 13 or more primer pairs to produce an amplified mixture of nucleic acid-target regions containing a polymorphic loci; contacting the amplified mixture of nucleic acid-target regions with 13 or more genotyping primers in the presence of at least one chain terminating reagent under primer mass extension conditions whereby the primers are extended up to, or through, the respective polymorphic loci, wherein there is one genotyping primer for each polymorphic loci within a nucleic acid-target molecule; and determining the mass of the extended genotyping primers, wherein at least 60% of the genotypes for said 13 or more nucleic acid target-regions attempted are determined.

Also provided are multiplex methods of genotyping a plurality of polymorphic loci, comprising: simultaneously amplifying a plurality of nucleic acid-target regions under amplification conditions whereby at least 60% of 7 or more nucleic acid target-regions attempted are amplified by 7 or more primer pairs to produce an amplified mixture of nucleic acid-target regions containing a polymorphic loci, wherein the amplification conditions comprise dNTPs and $MgCl_2$, and wherein the free Mg2+ concentration is between 1.0-2.0 mM; contacting the amplified mixture of nucleic acid-target regions with 7 or more genotyping primers in the presence of at least one chain terminating reagent under primer mass extension conditions whereby the primers are extended up to, or through, the respective polymorphic loci, wherein there is one genotyping primer for each polymorphic loci within a nucleic acid-target molecule; and determining the mass of the extended genotyping primers, wherein at least 60% of the genotypes for said 7 or more nucleic acid target-regions attempted are determined. In other embodiments, the quantity of primary and secondary primer pairs can be selected from 8 or more, 9 or more, 10 or more, 11 or more, 12 or more, or 13 or more.

In certain embodiments of each of these methods described above, a sequence tag is attached to the 5' end of either one or both primers of each primer pair. In other embodiments, the methods for performing multiplexed detection of a plurality of sequence variations are conducted using conditions (such as the amplification-reaction conditions and/or primer mass extension reaction conditions provided herein) that permit at least 65%, 70%, 75%, 80%, 85%, 90%, 91%, 92%, 93%, 94%, 95%, 96%, 97%, 98% or 99%, up to 100% of the attempted genotypes to be determined (i.e., are called). The conditions provided herein apply to numerous multiplexed reactions of 7-plex or more amplification reactions using a variety of amplification primer pairs and from a variety of target nucleic acids. In addition, all of the optimized amplification and/or primer mass extension genotyping reactions are applicable to multiplex assays ranging from 2-plex up to 6-plex and beyond, as described herein.

In particular embodiments, a sequence tag is attached to a plurality of primary and secondary primer pairs selected from 13 or more, 14 or more, 15 or more, 16 or more, 17 or more, 18 or more, 19 or more, or 20 or more, 21, 22, 23, 24, 25, 26, 27, 28, 29, 30, 35, 40, 45, or 50 or more primary and secondary primer pairs. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50 nucleotides in length, with a sequence tag of 10-mer length being particularly useful in the methods provided herein. The sequence tag need not be the same sequence for each primer pair in the multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer, such as -ACGTTGGATG- (hME-10; SEQ ID No:37), and is attached to the 5' end of each primary and secondary primer. In particular embodiments of the methods provided herein, only a single primer pair is used to amplify each particular nucleic acid target-region.

In one embodiment, the amplification-reaction conditions for the methods described above comprise water, genomic DNA, a buffer, dNTPs, the primary and secondary primer pairs, $MgCl_2$, and a polymerase, wherein the ratio of the concentration of $MgCl_2$ to the concentration of each one of the dNTPs is selected from $\leq 10:1$, $\leq 9:1$, $\leq 8:1$, $\leq 7:1$, $\leq 6:1$, or $\leq 5:1$. In a particular embodiment, the ratio of the concentration of $MgCl_2$ to the concentration of each one of the dNTPs is $\leq 7:1$. In other embodiments, the amplification-reaction conditions comprise between about 400-700 μM, between about 500-600 μM, or about 500 μM of each dNTP, along with about 50-250 nM primer pairs. In these embodiments, the total $MgCl_2$ concentration can be between about 2.6 mM up to about 4.8 mM $MgCl_2$, between about 3.0 up to about 4.5 mM $MgCl_2$, and between about 3.5 mM up to about 4.0 mM $MgCl_2$. An important consideration when selecting the concentrations of the dNTPs and $MgCl_2$ to use, is that the free Mg2+ concentration should be kept between 1-2 mM. As used herein, the Free Mg2+ concentration=Total Mg2+ concentration (e.g., total [$MgCl_2$])–Total dNTP concentration for all 4 dNTPs (e.g., 200 μM each dNTP=800 μM total [dNTP]). In certain embodiments, the free Mg2+ is between 1.1-1.9 mM, between 1.2-1.8 mM, between 1.3-1.7 mM, between 1.4-1.6 mM. In a particular embodiment the free Mg2+ concentration is about 1.5 mM. For each of these methods, the multiplicity of amplification thermocycles can be about 45. In a particular embodiment, the amplification-reaction conditions comprise about 500 μM of each dNTP, about 100 nM primer pairs, and about 3.5 mM $MgCl_2$. For each of these methods, the multiplicity of amplification thermocycles can be about 45. For each of these methods the polymerase can be a Taq polymerase (such as HOTSTARTAQ®, available from QIAGEN®) at a concentration of 0.03 units/μl. In particular embodiments of the methods provided herein, the amplification-reaction conditions exclude the addition of one or any combination of the following additives selected from BSA (bovine serum albumin), glycerol, DMSO (dimethyl sulfoxide), urea or Q-SOLUTION®.

The genotyping primers hybridize adjacent to the sequence variation and the mixture further comprises a preselected combination of dNTPs and ddNTPs. In the preselected combination of dNTPs and ddNTPs, when a ddNTP is present in the mixture the same dNTP is absent. For these methods, the multiplicity of primer mass extension thermocycles is selected from at least about 60, 65, 70, 75, 80, 85, 90, 95, 100 or more. In one embodiment, the primer mass extension-reaction conditions comprise about 50 μM d/ddNTPs and about 1 μM genotyping primers. In certain embodiments for these primer mass extension reactions, the primer mass extension-reaction conditions further comprise about 0.05 up to about 0.5 Units DNA polymerase per microliter. In other embodiments, the primer mass extension-reaction conditions further comprise about 0.1 up to about 0.3 Units DNA polymerase per microliter. In other embodiments, the primer mass extension-reaction conditions further comprise about 0.14 up to about 0.2 Units DNA polymerase per microliter. In a particular embodiment, the primer mass extension-reaction conditions further comprise about 0.14 Units DNA polymerase per microliter.

In some embodiments, for at least one primer pair in the plurality of primer pairs, one primer is in lower concentration than the other primer. Alternatively, for each of the plurality of primer pairs, one primer is in lower concentration than the other primer. In such embodiments, the lower concentration primer for a particular nucleic acid-target region can be in the same orientation as the genotyping primer for that nucleic acid-target region. Further, the amplified products of the amplifying step can be single-stranded nucleic acid molecules.

In other embodiments, provided herein are methods for performing multiplexed amplification of target nucleic acid, the method by designing 7 or more pairs of primary and secondary primers, wherein each primer pair amplifies a particular nucleic acid target-region on a target nucleic acid, forming a mixture containing the plurality of primer pairs and one or more target nucleic acids to amplify a plurality of nucleic acid target-regions, and subjecting the mixture to a multiplicity of thermocycles under amplification-reaction conditions that permit amplification of greater than 60% of the 7 or more nucleic acid target-regions. Also provided are methods for performing multiplexed amplification of target nucleic acid, the method by designing 8 or more pairs of primary and secondary primers, wherein each primer pair amplifies a particular nucleic acid target-region on a target nucleic acid, forming a mixture containing the plurality of primer pairs and one or more target nucleic acids to amplify a plurality of nucleic acid target-regions, and subjecting the mixture to a multiplicity of thermocycles under amplification-reaction conditions that permit amplification of greater than 60% of the 8 or more nucleic acid target-regions.

For example, provided are methods for performing multiplexed amplification of target nucleic acid, the method comprising: a) designing 7 or more pairs of primary and secondary primers, wherein each primer pair amplifies a particular nucleic acid target-region on a target nucleic acid; b) forming a mixture containing the plurality of primer pairs and one or more target nucleic acids to amplify a plurality of nucleic acid target-regions; and c) subjecting the mixture of step b) to a multiplicity of thermocycles under amplification-reaction conditions that permit amplification of greater than 60% of the 7 or more nucleic acid target-regions, wherein only a single primer pair is used to amplify each particular nucleic acid target-region. In other embodiments, the quantity of primary and secondary primer pairs can be selected from 8 or more, 9 or more, 10 or more, 11 or more, 12 or more, or 13 or more.

Also provided are methods for performing multiplexed amplification of target nucleic acid, the method comprising: a) designing 13 or more pairs of primary and secondary primers, wherein each primer pair amplifies a particular nucleic acid target-region on a target nucleic acid; b) forming a mixture containing the plurality of primer pairs and one or more target nucleic acids to amplify a plurality of nucleic acid target-regions; and c) subjecting the mixture of step b) to a multiplicity of thermocycles under amplification-reaction conditions that permit amplification of greater than 60% of the 13 or more nucleic acid target-regions.

Also provided are methods for performing multiplexed amplification of target nucleic acid, the method comprising: a) designing 7 or more pairs of primary and secondary primers, wherein each primer pair amplifies a particular nucleic acid target-region on a target nucleic acid; b) forming a mixture containing the plurality of primer pairs and one or more target nucleic acids to amplify a plurality of nucleic acid target-regions; and c) subjecting the mixture of step b) to a multiplicity of thermocycles under amplification-reaction conditions that permit amplification of greater than 60% of the 7 or more nucleic acid target-regions, wherein the amplification-reaction conditions comprise dNTPs and $MgCl_2$, and wherein the free Mg2+ concentration is between 1.0-2.0 mM (e.g., 1.1, 1.2, 1.3, 1.4, 1.5, 1.6, 1.7, 1.8, 1.9). In other embodiments, the quantity of primary and secondary primer pairs can be selected from 8 or more, 9 or more, 10 or more, 11 or more, 12 or more, or 13 or more.

In certain embodiments of each of these methods described above, a sequence tag is attached to the 5' end of either one or both primers of each primer pair. In other embodiments, the amplification-reaction conditions provided herein permit amplification of a percentage of the 7 or more nucleic acid target-regions selected from greater than 60%, 65%, 70%, 75%, 80%, 85%, 90%, 91%, 92%, 93%, 94%, 95%, 96%, 97%, 98% or 99%, up to 100% of the 7 or more nucleic acid target-regions. The conditions provided herein apply to numerous multiplexed reactions of 7-plex or more amplification reactions using a variety of amplification primer pairs and from a variety of target nucleic acids.

In particular embodiments, a sequence tag is attached to a plurality of primary and secondary primer pairs selected from 13 or more, 14 or more, 15 or more, 16 or more, 17 or more, 18 or more, 19 or more, or 20 or more, 21, 22, 23, 24, 25, 26, 27, 28, 29, 30, 35, 40, 45, or 50 or more primary and secondary primer pairs. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50 nucleotides in length, with a sequence tag of 10-mer length being particularly useful in the methods provided herein. The sequence tag need not be the same sequence for each primer pair in the multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer, such as -ACGTTGGATG- (hME-10; SEQ ID No:37), and is attached to the 5' end of each primary and secondary primer. In particular embodiments of the methods provided herein, only a single primer pair is used to amplify each particular nucleic acid target-region.

In one embodiment, the amplification-reaction conditions for the methods described above comprise water, genomic DNA, a buffer, dNTPs, the primary and secondary primer pairs, $MgCl_2$, and a polymerase, wherein the ratio of the concentration of $MgCl_2$ to the concentration of each one of the dNTPs is selected from $\leq 10:1$, $\geq 9:1$, $\leq 8:1$, $\leq 7:1$, $\leq 6:1$, or $\leq 5:1$. In a particular embodiment, the ratio of the concentration of $MgCl_2$ to the concentration of each one of the dNTPs is $\leq 7:1$. In other embodiments, the amplification-reaction conditions comprise between about 400-700 µM, between about 500-600 µM, or about 500 µM of each dNTP, along with about 50-250 nM primer pairs. In these embodiments, the total $MgCl_2$ concentration can be between about 2.6 mM up to about 4.8 mM $MgCl_2$, between about 3.0 up to about 4.5 mM $MgCl_2$, and between about 3.5 mM up to about 4.0 mM $MgCl_2$. An important consideration when selecting the concentrations of the dNTPs and $MgCl_2$ to use, is that the free Mg2+ concentration should be kept between 1-2 mM. As used herein, the Free Mg2+ concentration=Total Mg2+ concentration (e.g., total [$MgCl_2$])-Total dNTP concentration for all 4 dNTPs (e.g., 200 µM each dNTP=800 µM total [dNTP]). In certain embodiments, the free Mg2+ is between 1.1-1.9 mM, between 1.2-1.8 mM, between 1.3-1.7 mM, between 1.4-1.6 mM. In a particular embodiment the free Mg2+ concentration is about 1.5 mM. For each of these methods, the multiplicity of thermocycles can be 45. In a particular embodiment, the amplification-reaction conditions comprise about 500 µM of each dNTP, about 100 nM primer pairs, and about 3.5 mM $MgCl_2$. For each of these methods, the multiplicity of amplification thermocycles can be 45. For each of these methods the polymerase can be a Taq polymerase (such as HOTSTARTAQ®, available from QIAGEN®) at a concentration of 0.03 units/µl. In particular embodiments of the methods provided herein, the amplification-reaction conditions excludes the addition of one or any combination of the following additives selected from BSA, glycerol, DMSO, urea or Q-SOLUTION®.

In some embodiments, for at least one primer pair in the plurality of primer pairs, one primer is in lower concentration than the other primer. Alternatively, for each of the plurality of primer pairs, one primer is in lower concentration than the other primer. In such embodiments, the lower concentration primer for a particular nucleic acid-target region can be in the same orientation as the genotyping primer for that nucleic acid-target region. Further, the amplified products of the amplifying step can be single-stranded nucleic acid molecules.

BRIEF DESCRIPTION OF THE DRAWINGS

FIG. 1 shows a multiplexed Homogeneous primer mass extension reaction.

DETAILED DESCRIPTION

1. Definitions

Unless defined otherwise, all technical and scientific terms used herein have the same meaning as is commonly understood by one of skill in the art to which the invention(s) belong. All patents, patent applications, published applications and publications, GENBANK® sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the term "amplifying" or "amplification" refers to means for increasing the amount of a biopolymer, especially nucleic acids. Based on the 5' and 3' primers that are chosen, amplification also serves to restrict and define a target-region or locus of the genome which is subject to analysis. Amplification can be by any means known to those skilled in the art, and in particular embodiments, includes the use of the polymerase chain reaction (PCR). The phrase simultaneous amplification refers to the amplification of 2 or more nucleic acid target-regions at the same time. The simultaneous amplification is typically within the same amplification mixture.

As used herein, the term "multiplexing" refers to the simultaneous amplification or primer mass extension reaction of more than one oligonucleotide or primer (e.g., in a single reaction container); or the simultaneous analysis of more than one oligonucleotide, in a single mass spectrometric or other mass measurement, i.e., a single mass spectrum or other method of reading sequence.

As used herein, the phrase "simultaneous amplification" refers to the multiplexed amplification of 2 or more loci or nucleic acid target-regions in a single reaction mixture. Simultaneous amplification therefore encompasses 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, amplification reactions. The amplification of each particular target-region occurs in parallel at the same time. Although it is contemplated herein that the simultaneous amplifications can occur in separate reaction mixtures, for the methods provided herein the simultaneous amplification reactions typically occur in the same single reaction. Likewise multiplexed primer mass extension refers to the simultaneous extension of 2 or more genotyping primers in a single reaction mixture. Accordingly, multiplexed primer mass extension therefore encompasses 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, primer mass extension reactions. Multiplexed amplification and primer mass extension reactions also encompass 21, 22, 23, 24, 24, 25, 26, 27, 28, 29, 30, 35, 40, 45, or 50 or more reactions.

As used herein, the term "sequence tag" refers to any oligonucleotide sequence that is attached to the 5' ends of the PCR amplification primer used herein, so long as the particular sequence tag does not form secondary structures or does not contain significant homology to the genome. The sequence tag is not necessary for amplification. The sequence tags used herein can range from 5 up to 20, from 5 up to 30, from 5 up to 40, or from 5 up to 50 nucleotides in length, with a sequence tag of 10-mer length being particularly useful in the methods provided herein. In a particular embodiment, the sequence tag used herein corresponds to the 10-mer 5'-ACGTTGGATG- (referred to as hME-10; SEQ ID No:37). In the homogeneous methods provided herein, the sequence tags are typically added to the primary and secondary primers, and to a least the primary primers. The sequence tags function to increase the mass of the unused amplification primer so it falls outside the mass range of analytical peaks; and to balance amplification.

As used herein, the phrases "pairs of primary and secondary primers" or "primer pair," or grammatical variations thereof, refers to pairs of forward and reverse primers used to amplify a particular target-region (loci) from a particular target nucleic acid.

As used herein, the term "amplifies" refers to increasing the number of copies of a particular nucleic acid target-region of a target nucleic acid.

As used herein, the phrase "target nucleic acid" refers to one or more nucleic acids, such as genomic DNA, from which one or more regions or loci are to be amplified.

As used herein, the phrase "nucleic acid-target region" refers to the region-specific areas or loci of a target nucleic acid that are amplified for subsequent sequence variation analysis. The amplified nucleic acid-target regions each contain at least one polymorphic loci or site that is being genotyped.

As used herein, the phrase "amplified mixture of nucleic acid-target regions" refers to the mixture that result from simultaneously amplifying more than one (i.e., a plurality) nucleic acid target-region, whereby each target-region amplified is present in a substantially increased number of copies.

As used herein, the phrase "a multiplicity of thermocycles" refers to the well-known technique of temperature cycling a particular biological reaction. Exemplary temperature cycles are set forth herein in the Examples.

As used herein, the phrase "under amplification-reaction conditions whereby at least 60% of the 7 or more nucleic acid target-regions attempted are amplified by 7 or more primer pairs," or grammatical variations thereof, refers to providing particular combinations of reagents in the multiplexed reaction mixture, such that a higher percentage of the desired loci or nucleic acid target-regions are amplified. In certain other embodiments, these reaction conditions permit amplification of a percentage of the 7 or more nucleic acid target-regions selected from greater than 50%, 60%, 70%, 75%, 85%, 90%, 91%, 92%, 93%, 94%, 95%, 96%, 97%, 98% or 99%, up to 100% of the 7 or more nucleic acid target-regions. For example, the amplification of 90% of 10 target loci where 10 primary and secondary primer pairs are used results in 9 targets amplified; the amplification of 50% of 50 target-regions where 50 or more pairs of primary and secondary primer pairs are used results in amplification of 25 target-regions; the amplification of 75% of 40 target-regions where 40 or more pairs of primary and secondary primer pairs are used results in amplification of 30 target-regions, and so on.

In one embodiment, the amplification-reaction conditions for the methods described above comprise water, genomic DNA, a buffer, dNTPs, the primary and secondary primer pairs, $MgCl_2$, and a polymerase, wherein the ratio of the concentration of $MgCl_2$ to the concentration of each one of the dNTPs is selected from $\leq 10:1$, $\leq 9:1$, $\leq 8:1$, $\leq 7:1$, $\leq 6:1$, or $\leq 5:1$. In a particular embodiment, the ratio of the concentration of $MgCl_2$ to the concentration of each one of the dNTPs is $\leq 7:1$. In other embodiments, the amplification-reaction conditions comprise between about 400-700 µM, between about 500-600 µM, or about 500 µM of each dNTP, along with about 50-250 nM primer pairs. In these embodiments, the total $MgCl_2$ concentration can be between about 2.6 mM up to about 4.8 mM $MgCl_2$, between about 3.0 up to about 4.5 mM $MgCl_2$, and between about 3.5 mM up to about 4.0 mM $MgCl_2$. An important consideration when selecting the concentrations of the dNTPs and $MgCl_2$ to use, is that the free Mg2+ concentration should be kept between 1-2 mM. As used herein, the Free Mg2+ concentration=Total Mg2+ concentration (e.g., total $[MgCl_2]$)–Total dNTP concentration for all 4 dNTPs (e.g., 200 µM each dNTP=800 µM total [dNTP]). In certain embodiments, the free Mg2+ is between 1.1-1.9 mM, between 1.2-1.8 mM, between 1.3-1.7 mM, between 1.4-1.6 mM. In a particular embodiment the free Mg2+ concentration is about 1.5 mM.

In another embodiment particular, the amplification-reaction conditions comprise about 500 µM dNTPs, about 100 nM primer pairs, and about 3.5 mM $MgCl_2$. In a particular embodiment, the reaction reagents and conditions set forth in Table 4 are used to amplify greater than 70% of the total nucleic acid target-regions, when sequence tags are not used; and greater than 90% of the total nucleic acid target-regions, when sequence tags (e.g., hME-10) are used on all primers.

As used herein, the phrase "wherein only a single primer pair is used to amplify each particular nucleic acid target-region" refers to using, in a single amplification reaction, only a single primer pair to amplify the respective particular nucleic acid target-region, as opposed to using two or more primer pairs in the same reaction (e.g., 2-stage or 2-step PCR, such as one primer pair without tags and one with tags, etc.) directed to the same nucleic acid target-region. For example, to amplify 12 nucleic acid target-regions, only 12 primer pairs are used; one primer pair for each respective nucleic acid target-region.

For the PCR amplification methods provided herein that are specifically combined with genotype determination using subsequent primer mass extension reactions with mass spectrometry, when the subsequent primer mass extension reaction mixture comprises each of the 4 different chain terminating reagents (e.g., all 4 ddNTPs, e.g., ddATP, ddTTP, ddGTP and ddCTP), then only a single primer pair is used to amplify each particular nucleic acid target-region.

For each of the other PCR amplification methods provided herein that are specifically combined with genotype determination using subsequent primer mass extension reactions with mass spectrometry, when the subsequent primer mass extension reaction mixture comprises at least one dNTP, and therefore 3 or fewer chain terminating reagents (e.g., ddNTPs, ddATP, ddTTP, ddGTP and ddCTP), then either a single primer pair, or more than one primer pair (e.g., 2-stage PCR), can be used to amplify each particular nucleic acid target-region.

For each of the other PCR amplification methods provided herein that are specifically combined with genotype determination using subsequent primer mass extension reactions with mass spectrometry, when the method is directed to 13-plex up to 50-plex or higher amplification reactions (e.g., using 13 or more primary and secondary primer pairs), then either a single primer pair, or more than one primer pair (e.g., 2 primer pairs as in 2-stage PCR), can be used to amplify each particular nucleic acid target-region.

For each of the other PCR amplification methods provided herein that specifically require combination with genotyping using subsequent primer mass extension reactions with mass spectrometry, when the method requires a particular free Mg2+ concentration between 1.0-2.0 mM (or requires any other particular reagent condition set forth in Table 4 herein), then either a single primer pair, or more than one primer pair, can be used to amplify each particular nucleic acid target-region.

For the PCR amplification methods provided herein that do not specifically require combination with genotype determination using subsequent primer mass extension reactions with mass spectrometry, when the method is directed to 12-plex or fewer amplification reactions (e.g., 2-plex, 3-plex, 4-plex, 5-plex, 6-plex, 7-plex, 8-plex, 9-plex, 10-plex, 11-plex), then only a single primer pair is used to amplify each particular nucleic acid target-region. In another embodiment of the PCR amplification methods provided herein that does not specifically require genotyping using subsequent primer mass extension reactions with mass spectrometry, when the method is directed to 13-plex up to 50-plex or higher amplification reactions, then either a single primer pair, or more than one primer pair (e.g., 2-stage PCR), can be used to amplify each particular nucleic acid target-region. In other words, the amplification reaction can encompass in the same reaction mixture, either only a single PCR primer pair, or more than one PCR primer pair, designed to amplify the same nucleic acid target-region. When 2 or more primer pairs are used in the methods provided herein, each primer pair can be added to the PCR reaction mixture simultaneously or sequentially (e.g., the first primer pair for the first 5-15 thermocycles and then add the second primer pair for the remainder of the thermocycles of the amplification reaction).

As used herein, the phrase "sequence variation" or "polymorphism" refers to the coexistence of more than one form or allele of a nucleic acid, such as a chromosome, or portion thereof, or a gene or portion thereof. For example, a portion or locus of a gene at which there are at least two different alleles, i.e., two different nucleotide sequences, is referred to as a polymorphic loci, site or region of a gene. A polymorphic loci can be a single nucleotide (e.g., SNP) or can be several nucleotides in length (e.g., insertions or deletions). Accordingly, polymorphism includes substitutions, insertions, duplications and deletions of nucleotides. A polymorphism can also refer to a particular nucleotide(s) or nucleotide sequence occurring at a particular polymorphic site.

As used herein, the term "genotyping" refers to the process of determining the particular nucleotide or nucleotides (e.g., sequence variation) either present or absent at a particular polymorphic loci. In the context of the optimized hME reactions provided herein, obtaining a genotype by PCR amplification of a target in combination with a primer mass extension reaction and mass spectrometry analysis corresponds to obtaining a "call" of the respective sequence variation (polymorphic loci). As used herein, the term "call rate" or "calling rate" refers to the number of calls (e.g., genotypes determined) obtained relative to the number of calls attempted to be obtained. In other words, for a 12-plex hME reaction, if 10 genotypes are ultimately determined from the mass spectra after the PCR amplification and primer mass extension reactions, then 10 calls have been obtained with a call rate of 10/12.

As used herein, the phrase "dephosphorylating unincorporated deoxynucleotides from the amplification reaction" refers to a step in the process prior to the primer mass extension reaction where the remaining nonincorporated dNTPs from the PCR amplification reaction are inactivated and/or removed. Shrimp alkaline phosphatase (SAP) is typically used for this step, as described herein.

As used herein, the phrase "forming a mixture of genotyping primers suitable to genotype each sequence variation of said plurality of nucleic acid target-regions" refers to the design and preparation of a mixture containing a plurality of 7, 8, 9, 10, 11, 12, 13, 14, 15, 16, 17, 18, 19, 20, 21, 22, 23, 24, 25, 26, 27, 28, 29, 30, 35, 40, 45, 50 or more genotyping primers used to genotype each sequence variation in the multiplexed reaction. For example, for a 15-plex multiplex primer mass extension assay, there are 15 genotyping primers in the mixture; for a 20-plex there are 20 genotyping primers in the mixture, etc. Once the genotyping primers have been selected, the primer concentrations in the primer mass extension primer mix can be adjusted for each multiplex by first preparing a mix of all the primer mass extension primer mass extension primers needed. Using MALDI-TOF-MS, analyze a 360 nM dilution of the primer mix previously desalted. Check whether the primer peaks in the mass spectrum have comparable heights. If all peaks are at least 50% of the height of the highest peak, they are acceptable. If any peak is less than 50% of the height of the highest peak, add more of the primer having the short peak. Once the concentrations of the primers have been adjusted in the primer mix to even out peak heights, use the adjusted primer mix in the actual primer mass extension assay run.

As used herein, the phrase "contacting the amplified mixture of nucleic acid-target regions with 7 or more genotyping primers" refers to the combining of the PCR amplification reaction product containing the plurality of amplified nucleic acid target-regions with a mixture containing 7 or more genotyping primers. Once combined each genotyping primer will hybridize adjacent to the respective sequence variation for subsequent primer extension. For example, typically where 10 nucleic acid-target regions are attempted for amplification, there are 10 genotyping primers used in the primer mass extension reactions. Also contemplated herein are embodiments where a single amplified nucleic acid-target region contains 2, 3, 4, 5, 6, 7, 8, 9, 10, 11, 12, 13, 14, 15 or more polymorphic loci therein. Where there are 2 or more polymorphic loci contained on a single amplified nucleic acid-target region, then 2 or more genotyping primers will be contacted with that particular nucleic acid-target region. For example, where 2 amplified nucleic acid-target regions each contain 5 polymorphic therein, then the amplified mixture of 2 nucleic acid-target regions will be contacted with 10 genotyping primers, and so on.

As used herein, the phrase "under primer mass extension-reaction conditions whereby the genotyping primers are extended up to, or through, the respective polymorphic loci," or grammatical variations thereof, refers to the well-known process of thermocycling a primer mass extension reaction mixture through various temperature settings, such as described in Example 2 herein, to achieve multiple primer mass extension reactions. In particular embodiments of the methods provided herein, the multiplicity of primer mass extension thermocycles can be selected from at least about 50, 60, 65, 70, 75, 80, 85, 90, 95, 100 or more. The termination mixes typically comprised of chain terminating reagents corresponding to ddNTPs along with dNTPs are selected such that two distinct extension products are created that differ in length in an allele-specific manner, thus creating mass separations between alleles equal to the mass of a nucleotide. One of the two extension products terminates at the polymorphic site (i.e., up to the sequence variation, or "Extension into SNP site" at FIG. 1), whereas the other extension product is extended through the polymorphic site (i.e., "Extension past SNP site" in FIG. 1) and is then terminated.

As used herein, the phrase "in the presence of at least one deoxynucleotide and at least one chain terminating reagent" or grammatical variations thereof, such as "the presence of four different chain terminating reagents," and "at least one chain terminating reagent" refers to the specified number of deoxynucleotides or chain terminating reagents being present in the reaction mixture where the amplified nucleic acid-target regions are contacted with the genotyping primers. A chain terminating reagent refers to any compound that can be incorporated into an oligonucleotide primer by a suitable polymerase whereby primer extension is halted by the chain terminating reagent at the nucleotide site of incorporation. Exemplary chain terminating reagents for use herein include the dideoxynucleotides (ddNTPs, ddATP, ddTTP, ddGTP or ddCTP). The term deoxynucleotide(s) refers to any one or more of the well-known dNTPs, such as dATP, dTTP, dGTP, or dCTP.

As used herein, the phrase "desalting the reaction product of the primer mass extension step," refers to a desalting step to cleanse the primer mass extension products prior to mass spectrometry analysis. One method of conducting the desalting step is set forth in Example 2.

As used herein, the phrase "determining the mass of the extended genotyping primers" refers to detecting the mass of the primer mass extension products using any suitable mass detection format known to those of skill in the art, such as for example, mass spectrometry. Such formats include, but are not limited to, Matrix-Assisted Laser Desorption/Ionization, Time-of-Flight (MALDI-TOF), Electrospray ionization (ESi), IR-MALDI (see, e.g., published International PCT application No. 99/57318 and U.S. Pat. No. 5,118,937), Orthogonal-TOF (O-TOF), Axial-TOF (A-TOF), Ion Cyclotron Resonance (ICR), Fourier Transform, Linear/Reflectron (RETOF), Quadrupole mass spectrometry, Quadrupole ion trap mass spectrometry, and combinations thereof. See also, Aebersold and Mann, Mar. 13, 2003, Nature, 422:198-207 (e.g., at FIG. 2); and Yates (1998) *J. of Mass Spec.* 33:1-19, for a review of exemplary methods for mass spectrometry suitable for use in the methods provided herein, which articles are incorporated herein in its entirety by reference. MALDI, particular UV and IR, and O-TOF are among the formats for mass spectrometry.

For example, O-TOF instruments possess a number of attributes inherent to their design which make them ideally suited for coupling liquid separation techniques to Atmospheric Pressure Ionization (API). The first attribute is the fast acquisition rates achieved by O-TOF. Acquisition rates on the order of 10's of milliseconds are not uncommon. Thus, narrow peaks (<1 second FWHM) associated with separation techniques such as capillary electrophoresis (CE) can be easily profiled. Along with fast scan rates, O-TOF mass spectrometers also has the ability to see a very broad mass range (e.g., 0-6000 Da/spectra). In addition, these instruments possess excellent sensitivity since all the ions entering the analyzer region are accelerated to the detector at high repetition rates (e.g., 5 kHz).

As used herein, the phrase "wherein at least 60% of the genotypes for said 7 or more nucleic acid target-regions attempted are determined," or grammatical variations thereof (such as 70, 80, 90%, etc. or 10 or more, 15 or more, 50 or more, etc.), refers to a call rate corresponding to the stated minimum percentage of the total number of polymorphic loci attempted for genotyping. These increased call rates (genotypes determined) are achieved by providing particular combinations of reagents and conditions in the multiplexed PCR and primer mass extension reaction mixtures, such that a minimum percentage of the desired loci or nucleic acid target-regions are: amplified, primer mass extended, and successfully detected by mass spectrometry. In other embodiments, this combination of reaction conditions results in a call rate percentage (e.g., % genotypes determined of those attempted) of the genotypes for number of nucleic acid target-regions attempted, that is at least 50%, 60%, 70%, 75%, 85%, 90%, 91%, 92%, 93%, 94%, 95%, 96%, 97%, 98% or 99%, up to 100% of the genotypes for the number of nucleic acid target-regions attempted (plex). The multiplex number of nucleic acid target-regions attempted for amplification and genotyping can be 7, 8, 9, 10, 11, 12, 13, 14, 15, 16, 17, 18, 19, 20, 25, 30, 35, 40, 45, 50 or more. For example, the successful calling of 90% of 10 polymorphic loci attempted for genotyping results in 9 genotypes determined; the successful calling of 80% of 50 polymorphic loci attempted for genotyping results in 40 genotypes determined; and so on.

As used herein, mass spectrum or mass spectra refers to the presentation of data obtained from analyzing a biopolymer or fragment thereof by mass spectrometry either graphically or encoded numerically.

As used herein, "allele", which is used interchangeably herein with "allelic variant" refers to alternative forms of a nucleic acid such as a gene or polymorphic regions thereof. Alleles occupy the same locus or position (referred to herein as a polymorphic region) on homologous chromosomes. When a subject has two identical alleles of a polymorphic region within a gene, the subject is said to be homozygous for the allele. When a subject has two different alleles of a polymorphic region within a gene, the subject is said to be heterozygous for the allele. Alleles of a specific gene can differ from each other at a polymorphic region corresponding to a single nucleotide, or several nucleotides, and can include substitutions, deletions, insertions and duplications of nucleotides. An allele of a gene can also be a form of a gene containing a mutation.

As used herein, "genotype" refers to the identity of the alleles present in an individual or sample. The term "genotyping a sample" or "genotyping an individual" refers to determining a specific allele or specific nucleotide(s) in a sample or carried by an individual at particular region(s).

2. SNP Genotyping Methods Using MALDI-TOF MS Detection 2.1. Homogeneous Primer Mass Extension (hME) Assay The homogeneous primer mass extension (hME) assay is a single-tube reaction carried out in solution without using any immobilization step. Initially, genomic sequences (nucleic acid target-regions) containing polymorphisms or mutations are PCR-amplified in a reaction including two sequence-specific primers (PCR-For and -Rev; also referred to herein as a primary and secondary primer pair). For the multiplexed homogeneous primer mass extension assays provided herein, a plurality of primer pairs are used (e.g., 7, 8, 9, 10, 11, 12, 13, 14, 15, 16, 17, 18, 19 or 20 or more primer pairs). After the PCR, a dephosphorylation step with shrimp alkaline phosphatase (SAP) is used to destroy the remaining free dNTPs in the solution. A homogenous mass extension reaction (hME)

is then performed in 45 cycles of denaturation, primer annealing and primer mass extension, by varying the temperature (also referred to herein as thermocycling). The products are desalted, such as for example, by adding a suspension of cation exchange beads ($NH_4^+$ form). After a brief centrifugation, the supernatant is used for MALDI-TOF MS analysis. hME is easily compatible with automated liquid handling stations and thermal cyclers currently available because it requires only liquid addition steps throughout the whole procedure. The amount of products can also exceed the amount of template since the hME cycling amplifies the products linearly and they remain in the solution.

In the methods provided herein, the desalting step is important because the purity of the products directly affects the success of MALDI-TOF MS. In addition to the desalting step, the PCR conditions have been optimized herein (as set forth in the Examples) to achieve a high level of multiplexed PCR amplification, while at the same time, not adversely impacting the quantity and quality of the results obtained by mass spectrometry analysis of the primer mass extension products. For example, particular amounts of $MgCl_2$ concentrations have been identified herein that permit high levels (e.g., 7-plex up to 50-plex or more) of multiplexed PCR and primer mass extension reactions along with successful mass spectrometry analysis. For example, in particular embodiments, the amplification-reaction conditions comprise water, genomic DNA, a buffer, dNTPs, the primary and secondary primer pairs, $MgCl_2$, and a polymerase, wherein the ratio of the concentration of $MgCl_2$ to the concentration of each one of the dNTPs is selected from $\leq 10:1$, $\leq 9:1$, $\leq 8:1$, $\leq 7:1$, $\leq 6:1$, or $\leq 5:1$. In a particular embodiment, the ratio of the concentration of $MgCl_2$ to the concentration of each one of the dNTPs is $\leq 7:1$. In other embodiments, the amplification-reaction conditions comprise between about 400-700 µM, between about 500-600 µM, or about 500 µM of each dNTP, along with about 50-250 nM primer pairs. In these embodiments, the total $MgCl_2$ concentration can be between about 2.6 mM up to about 4.8 mM $MgCl_2$, between about 3.0 up to about 4.5 mM $MgCl_2$, and between about 3.5 mM up to about 4.0 mM $MgCl_2$. An important consideration when selecting the concentrations of the dNTPs and $MgCl_2$ to use, is that the free $Mg^{2+}$ concentration should be kept between 1-2 mM. As used herein, the Free $Mg^{2+}$ concentration=Total $Mg^{2+}$ concentration−Total dNTP concentration for all 4 dNTPs. In certain embodiments, the free $Mg^{2+}$ is between 1.1-1.9 mM, between 1.2-1.8 mM, between 1.3-1.7 mM, between 1.4-1.6 mM. In a particular embodiment the free $Mg^{2+}$ concentration is about 1.5 mM. For each of these methods, the multiplicity of amplification thermocycles can be about 45. In a particular embodiment of the methods provided herein, as set forth in Table 4, the amplification-reaction conditions comprise about 500 µM of each dNTP, about 100 nM primer pairs, and about 3.5 mM $MgCl_2$. For each of these methods, the multiplicity of amplification thermocycles can be 45.

Other PCR amplification conditions have been identified herein that increase the subsequent genotyping performance of multiplex primer mass extension reactions in combination with mass spectrometry analysis (i.e., hME). For example, the PCR buffer concentration of the HOTSTARTAQ® PCR buffer containing 15 mM $MgCl_2$ (10×) should not exceed 1.25× because higher salt concentrations have been found to negatively affect the hME multiplex reactions by inhibiting the DNA polymerase (e.g., THERMO SEQUENASE™ DNA polymerase set forth in the optimized hME reaction mix of Table 5). In addition, in particular embodiments, these conditions encompass the exclusion of any one or combination of the suggested PCR additives BSA, glycerol, DMSO, urea and/or Q-SOLUTION® from PCR amplification reaction. The Q-SOLUTION® (commercially available from QIAGEN®) is a suggested PCR additive for use with QIAGEN's HOTSTARTAQ® PCR buffer and the HOTSTARTAQ® polymerase. Q-SOLUTION® is stated to facilitate amplification of difficult templates by modifying the melting behavior of DNA. The use of Q-SOLUTION® is stated to improve suboptimal PCR. Unlike DMSO and other PCR additives, the Q-SOLUTION® is used at a defined working concentration with any primer-template system and is not toxic. In the PCR amplification reaction methods provided herein, the Q-SOLUTION® should not be used because it has a negative effect on the subsequent MALDI-TOF MS analysis of the hME genotyping primers. Thus, in particular embodiments of each of the methods provided herein, the PCR amplification-reaction conditions explicitly exclude the addition of one or any combination, including all, of the following additives selected from BSA, glycerol, DMSO, urea or Q-SOLUTION®.

2.2. Multiplexing

The typical mass range of primer-extension products is between 5,000 Da to 10,000 Da, corresponding to 17-nt to 33-nt in length. This provides a wide window for multiplexing since primer mass extension primers targeting different SNPs can be chosen so that all extended products and primers do not overlap in the mass spectrum. The mass separation among peaks of uniplex reactions is at least one base (~300 Da). Due to the high accuracy of TOF mass spectrometers (~0.1% in linear mode), smaller mass difference can be unambiguously discriminated without running into the risk of peak mis-identification. Normally neighboring peaks with mass differences of 50 Da are well separated in linear TOF instruments (requiring resolution of only 100 to 160) and require a mass accuracy of only 0.625% to 1% for identification. Fifty Dalton has therefore previously been used as the minimum requirement for mass spectra peak separations in multiplex reactions.

In particular embodiments of the multiplexing embodiments provided herein, a strategy (referred to as the 30/20 strategy) has been employed that uses 20 dalton minimum mass spectra peak separation. As used herein, the term "30/20" refers to the Unknown (+/− of analytes) and the Min Separation (Da) settings on the By-product Contaminants dialog box and the main MASSARRAY® Assay Design window, respectively. Accordingly, "30" is entered in the By-product Contaminants dialog box and "20" is entered into the main MASSARRAY® Assay Design window. Additional information regarding the MASSARRAY® Assay Design software version 2.0 can be found in the MASSARRAY® *Design User's Guide*, version 2.0, March/2003 available from SEQUENOM, Inc. (San Diego, Calif.), which is incorporated herein by reference in its entirety.

In the methods provided herein, multiplexing also starts at the PCR amplification level, which requires careful primer design. Automatic assay design software has been created to address the need for reliability and optimization simultaneously (described in section 3.1 herein). The need for real-time quality control for all assays in the mass spectrum of a multiplexed genotyping reaction has also prompted the development of real-time data acquisition software, which is discussed in 3.4.

Compared to gel electrophoresis, which lacks in resolution, and fluorescent detection, which has limited available wavelengths, MALDI mass spectrometry provides high resolution, high accuracy and wide mass range for designing highly multiplexed genotyping assays. The methods provided herein provide optimized nucleic acid target-region amplification and hME primer mass extension genotyping reaction conditions that have been optimized herein to permit moderate to high level multiplexing reactions (7-plex or higher) with greater efficiency and accuracy.

3. Automation for High Throughput Analysis

Although hardware and software available from SEQUENOM® are set forth herein, those of skill in the art will recognize that the optimized PCR and primer mass extension conditions provided for the multiplexing methods herein can be used with other combinations of hardware and software packages known to those of skill in the art for mass spectrometry analysis.

For example, among the issued patents and published international applications incorporated by reference herein, and that describe methods, systems and devices that can be adapted for use with the optimized multiplexing methods of genotyping provided herein, are: U.S. Pat. Nos. 5,807,522, 6,110,426, 6,024,925, 6,133,436, 5,900,481, 6,043,031, 5,605,798, 5,691,141, 5,547,835, 5,872,003, 5,851,765, 5,622,824, 6,074,823, 6,022,688, 6,111,251, 5,777,324, 5,928,906, 6,225,450, 6,146,854, 6,207,370, U.S. application Ser. No. 09/663,968, International PCT application No. WO 99/12040, WO 97/42348, WO 98/20020, WO 98/20019, WO 99/57318, WO 00/56446, WO 00/60361, WO 02/25567 and WO 02/086794. These patents and publications describe a variety of mass spectrometric analytical methods, substrates and matrices used in mass spectrometric analyses, and related methods and apparatus, including pin tools and other dispensing systems. It is intended that the methods, products and systems described in these patents and patent applications as well as other such methods that employ instruments for detection of molecules and computer-directed assays, and are particularly suitable for use in high throughput formats, can be adapted for use with the optimized multiplexing methods of genotyping provided herein. Other intended uses include any methods and assays that have an instrument for data acquisition and that employ data-typing analyses.

3.1. Assay Design

The process of assay design, presents two challenges. First, the design of PCR and extend primers will reliably amplify and interrogate a specific SNP site and the optimal multiplexing of assays is possible such that no single assay will fail due to competing kinetics or cross-hybridization reactions. Second, the products (analytes and by-products) are well resolved in the resulting mass spectra.

3.1.1. Assay Design for Primer Extension

To address the first challenge, mass extension and PCR primers can be designed to ensure amplification of the desired locus and to avoid other polymorphisms adjacent to the locus to be genotyped. Such primer design can be divided in to two steps. In the first step, potential primer sequences can be compared to genomic sequences to ensure that competing kinetics or cross-hybridization reactions will not occur. Comparison of a primer sequence to a genomic sequence can be accomplished by any method or software known in the art, including, for example BLAST®. Primer selection based on sequence comparison also can be accomplished by any method or software known in the art, for example PREXTEND (SEQUENOM®). In the second step, potential primer sequences can be compared to known polymorphism information (e.g., SNP database) to ensure that the primer does not hybridize to regions with known polymorphisms. Methods and software for comparing primer hybridization sites with known polymorphisms are known in the art, and can be performed using, for example PROXSNP (SEQUENOM®).

Mass extension primers also are designed with respect to target sequences of a given SNP strand such that the length must be between limits that can be, for example, user-specified (e.g., 17 to 24 bases or 17-26 bases) and must not contain any bases that are uncertain in the target sequence. The hybridization strength is gauged by calculating the sequence-dependent melting (or hybridization/dissociation) temperature, $T_m$. A particular primer choice may be disallowed, or penalized relative to other choices of primers, because of its hairpin potential, false priming potential, primer-dimer potential, low complexity regions, and problematic subsequences such as GGGG. Methods and software for designing mass extension primers according to these criteria are known in the art, and include, for example, SPECTRODESIGNER (SEQUENOM®).

For mass extension primer design there are two choices of primer sequence, adjacent to the SNP site on either side. These primers may be of various lengths, and each of these primer choices is scored using general primer design concerns and additional factors which are dependent on the set of extension products that result from employing each of the terminator mixes available. Generally, it is rare for SNP targets to fail at extend primer design on both sides of the SNP. The scores are mainly used to choose between alternative extend primer choices and terminator mixes (see, e.g., Table 1). Particular primer lengths for extend primers may not be suitable because of mass conflicts with contaminants (e.g., biotin-tags) or by-products (e.g., depurination products or, possibly, secondary extend-pausing products that are terminated by a dNTP instead of ddNTP). For example, an extension primer prematurely terminated with dA would have exactly the same mass as if normally terminated with ddG, and therefore these products are indistinguishable. To avoid miscalls in genotypes, such designs should not be chosen.

Table 1 provides the criteria for selecting an appropriate termination mix having 3 ddNTPs and 1 dNTP. Other termination mixes suitable for use herein can have all 4 ddNTPs with no dNTPs; can have 2 ddNTPs and 2 dNTPs; or can have 1 ddNTP and 3 dNTPs. Typically, primer mass extension assays are designed so that there are at least two dideoxy terminators present and at least one of the alleles is detected by a single base extension. Genotypes are called based on the differences between the masses of the terminators corresponding to the possible alleles. For instance, A/T extensions differ by 9 daltons (Da), the smallest mass difference possible; A/C differ by 24 Da; T/G differ by 25 Da; and C/G extensions differ by 40 Da, the largest mass difference. Unfortunately, some of these mass differences are close to the masses of possible ion adducts (Na: 23.0 Da; Mg: 24.3 Da; K: 39.1 Da), which can compromise interpretation of the spectra or require extra processing steps to minimize the occurrence of such adducts. One form of the primer mass extension assay described here avoids this issue by creating extension products that differ in length in an allele-specific manner, creating mass differences corresponding to the mass of a nucleotide (~300 Da) or more, far in excess of the shifts due to ion adducts. This is illustrated for a C/T polymorphism, for example, in FIG. 2 of Storm et al. (2003) *Methods in Mol. Biol.* 212:241-262. The differences in mass between the allele-specific extension products (and any unextended primer mass extension primer) is ~100 times greater than necessary to separate peaks in this portion of the mass spectrum. This makes distinguishing between the different alleles extremely easy.

In the methods provided herein, as set forth in the Storm et al. FIG. 2 illustration, the key design feature is the use of a terminator mix that yields extension products that differ in length in an allele-specific manner, thus creating mass separations between alleles equal to the mass of a nucleotide. In this example, a normal dG is used along with ddA, ddC, and ddT. For allele 1 (A1), the ddA is incorporated immediately, extending the primer, a 23-mer, to a 24-mer. For allele 2 (A2), the SNP calls for incorporation of the normal dG residue prior to incorporation of a ddA, extending the 23-mer primer to a 25-mer.

Occasionally, inappropriate extension products can occur by pausing of the polymerase after incorporation of one non-terminating nucleotide (i.e., dNTP), resulting in a prematurely terminated extension primer. The mass difference between this falsely terminated and a correctly terminated primer mass extension reaction at the polymorphic site is sometimes too small to resolve consistently and can lead to miscalls if an inappropriate termination mix is used. The mass differences between a false termination (i.e., one caused by pausing) and a correct termination must therefore be maximized to avoid making miscalls. Table 2 shows the mass differences that can result. It is best to avoid mass differences of $\leq 24$ Da.

TABLE 1

Selecting a termination mix

| SNP (Biallelic) | Termination Mix (dideoxynucleotides) |
|---|---|
| A/C | CGT (40 Da) |
| A/G | ACT (32 Da) |
| A/T | CGT (25 Da) |
| C/G | ACT (56 Da) |
|  | AGT (24 Da) |
| C/T | ACG (31 Da) |
| G/T | ACT (41 Da) |
| small ins/del | -dependent on sequence- |

Numbers in parentheses are the mass differences between a correct termination and a false termination (i.e., premature termination caused by pausing of the polymerase)

TABLE 2

Mass differences for pairs of nucleotides

|  |  | Deoxyribonucleotides | | | | Dideoxyribonucleotides | | | |
|---|---|---|---|---|---|---|---|---|---|
|  |  | dC | dT | dA | dG | ddC | ddT | ddA | ddG |
| ddNTPs* | ddC | NA | 31 | 40 | 56 | NA | 15 | 24 | 40 |
|  | ddT | 1 | NA | 25 | 41 | 15 | NA | 9 | 25 |
|  | ddA | 8 | 7 | NA | 32 | 24 | 9 | NA | 16 |
|  | ddG | 24 | 9 | 0 | NA | 40 | 25 | 16 | NA |

Note:
Differences in masses between a dideoxy- and a deoxy-nucleotide of the same base are not shown since a termination mix never contains both.
*Dideoxyribonucleotides For PCR primer design many more primers need to be evaluated but there is a greater chance of finding pairs of primers that satisfy optimal design parameters. Each potential primer is scored with respect to an optimal length (20 bases), an optimal $T_m$ (60° C., based, e.g., on the 4+2 rule), an optimal G-C content (50%), and, in some cases, an optimal amplicon length of 100 bp. Only primer pairs that would produce an amplicon length that satisfies the user-supplied minimum and maximum amplicon length bounds are suitable. The normalized combination of these scoring components is referred to as the uniplex PCR confidence score and is recorded in the output for successful assay designs. Methods and software for designing mass extension primers according to these criteria are known in the art, and include, for example, SPECTRODESIGNER (SEQUENOM®).

3.1.2. Assay Design for Mass Spectrometry

The second assay design challenge, resolution of products in resulting mass spectra, occurs with multiplexed assays. Design methods for achieving resolved mass spectra can include both primer design methods and reaction design methods. For primer design in multiplexed assays, the same general guideline for primer design applies such as avoiding false priming and primer dimers, only now more primers are involved. In addition, the analyte peaks in the mass spectra for one assay must be sufficiently well resolved from any product of any assay it is multiplexed with, including pausing peaks and any other user-specified by-product peaks. In addition, analyte peaks must fall within the user-specified mass window, for example, within a range of 5,000-8,500 Da. Methods and software for designing mass extension primers according to these criteria are known in the art, and include, for example, SPECTRODESIGNER (SEQUENOM®).

Efforts are also made to ensure that strong assays (i.e., assays yielding strong mass spectrometry peaks) are not multiplexed with weak assays (i.e., assays yielding weak mass spectrometry peaks) to avoid the respective analyte peaks appearing too unbalanced in the mass spectra. To avoid this, the primer concentrations can be adjusted as set forth in Example 2 herein. For example, in certain embodiments, the peaks in the mass spectrum for a multiplexed reaction may not have comparable heights. To improve the multiplexing results, it is recommended that the concentrations of hME primers are adjusted to even out peak heights (intensities) in the mass spectrum. Variations in peak height may stem from 1) inconsistent oligonucleotides quality and 2) unpredictable desorption/ionization behavior in MALDI. In an exemplary assay adjustment, a first mass spectrum that has peak A the highest, and peaks B, C and D are 40%, 30% and 20%, respectively, of the height of peak A, the amount of primers corresponding to peaks B, C, and D can be increased in the reaction mixture by 40%, 60% and 80%, respectively.

To adjust the primer concentrations in the primer mass extension primer mix, for each multiplex, prepare a mix of all the primer mass extension primer mass extension primers needed. Using MALDI-TOF-MS, analyze a 360 nM dilution of the primer mix previously desalted. Check whether the primer peaks in the mass spectrum have comparable heights. If all peaks are at least 50% of the height of the highest peak, they are acceptable. If any peak is less than 50% of the height of the highest peak, add more of the primer having the short peak. Once the concentrations of the primers have been adjusted in the primer mix to even out peak heights, use the adjusted primer mix in the actual primer mass extension assay run (see, e.g., Multiplex Primer Concentration Adjustment in Example 2).

3.2. Asymmetric PCR

In some embodiments, PCR primers can be used to amplify a nucleic acid-target region where the forward and reverse PCR primers are not present at the same concentration. PCR methods that use unequal primer concentrations are typically termed asymmetric PCR methods. Asymmetric PCR can be used to circumvent amplicon strand reannealing when, for example, a single strand of the amplicon is to be used in subsequent steps or methods.

Asymmetric PCR can be performed in the methods provided herein, typically in methods of amplifying a nucleic acid-target region to yield an amplified nucleic acid molecule, such as an amplified single-stranded nucleic acid molecule. In performing asymmetric PCR, upon depletion of the lower concentration primer, only extension of the higher concentration primer occurs, typically at a roughly linear rate. In the methods provided herein, the lower concentration primer of an asymmetric PCR method can be in the same orientation as the mass extension primer to be used in any subsequent mass extension steps or methods. For example, if the mass extension primer is a "forward" primer, the lower concentration asymmetric PCR primer typically also is a "forward" primer, and the higher concentration asymmetric PCR primer is a "reverse" primer, and vice versa. As a result, the single-stranded amplification product will be complementary to the mass extension primer. Such an asymmetric PCR method can thus generate single-stranded products that can be used in subsequent mass extension steps or methods.

Asymmetric PCR methods, when used, contain one lower concentration primer (LCP) and one higher concentration primer (HCP). The ratio of LCP:HCP can be any amount less than 1:1, and typically is 1:1.5, 1:2, 1:3, 1:4, 1:5, 1:6, 1:7, 1:8, 1:9, 1:10, 1:12, 1:15, 1:20, 1:25, 1:35, or 1:50, or about 1:1.5, 1:2, 1:3, 1:4, 1:5, 1:6, 1:7, 1:8, 1:9, 1:10, 1:12, 1:15, 1:20, 1:25, 1:35, or 1:50. Exemplary ratios of LCP:HCP are 1:5 and 1:10 (e.g., 100 nM:500 nM and 100 nm:1000 nM).

Any of a number of asymmetric PCR methods and variations thereof known in the art can be used herein, including, but not limited to, asymmetric PCR using nuclease-free polymerase or nuclease-resistant molecular beacons (see, e.g., U.S. Pat. Pub. No. 20030134307) and linear-after-the-exponential (LATE)-PCR (see, e.g., Sanchez et al., Proc. Natl. Acad. Sci. U.S. (2004) 101:1933-1938). For example, in LATE-PCR, the primers can be designed taking into account the effect of primer concentrations on primer $T_m$, using, for example, nearest-neighbor $T_m$ calculation methods, to yield a primer design in which primers have the same concentration-adjusted $T_m$.

3.3. Sample Preparation and Transfer

In particular embodiments, the samples are processed in microtiter plates (MTPs, 96 well or 384 well). For example, the PCR amplifications can be performed in either a PTC-225 DNA Engine TETRAD® thermo cycler (MJ RESEARCH, Watertown, Mass.) or a GENEAMP® PCR System 9700 (APPLIED BIOSYSTEMS®, Foster City, Calif.). Primer mass extension assays (either sME or hME) can be set up using an automated 96-channel pipette station (MULTI-MEK™, BECKMAN COULTER, Fullerton, Calif.; also available through SEQUENOM® as SPECTROPREP with customized add-ons and programs).

The primer mass extension products in each MTP can then be transferred to a silicon chip using different types of nano-dispensing devices. A four channel piezoelectric pipette (SPECTROJET, SEQUENOM®) is typically used for 96- and 384-well MTP. These piezoelectric tips are capable of dispensing sub-nanoliter volume per drop and are calibrated individually to dispense the same amount of analyte. The SPECTROJET is programmed to aspirate in parallel 1 µl of analyte from the MTP and dispense 14 nl in serial onto the corresponding pads on the silicon chip. The silicon chip (SPECTROCHIP® from SEQUENOM®) has a highly hydrophobic surface with 96 or 384 hydrophilic pads in an array format preloaded with 3-hydroxypicolinic acid (3-HPA) matrix. When dispensed, the aqueous analyte solution partially re-dissolves the matrix and the droplet quickly shrinks toward the hydrophilic pad and re-crystallize with the matrix within the 200×200 µm² pad. It has been found that the re-crystallized samples consistently yield better MALDI performance. The advantage of the piezoelectric pipette is the nature of non-contact dispensing which does not disturb the matrix crystals on the chip.

Nanoliter sample transfer can also be performed using very well-known pintool devices (such as SPECTROPOINT, available from SEQUENOM). In order to avoid destruction of matrix crystals upon contact dispensing, slot pins with openings bigger than 200 µm are used so that when the pins touch the chip surface, the matrix spot at center of the slot can be spared. The volume of liquid delivery has been found to be linear with the pin velocity upon contact, therefore it can be calibrated and precisely controlled. Since the pins can be mounted in an array format precisely with 4500±20 µm spacing, the pintool can be used to dispense analyte in parallel. By using 24 pins in a 4×6 array, the SPECTROPOINT is able to transfer 15 nl from a 384-well MTP to a 384-well chip in 12 minutes.

The advantage of using nanoliter sample preparation for MALDI mass spectrometry is that the miniaturized sample spot (200 µm×200 µm) provides more homogeneous sample distribution relative to the laser spot (d≈50-100 µm).

3.4. MALDI-TOF-MS

Most commercial TOF mass spectrometers can be modified to analyze a SPECTROCHIP® for use herein. This can be achieved by modifying the existing sample target to hold at least one chip, having a precise XY-stage, a customized geometry file that maps the array positions, and a sample vision system to monitor and align the array of spots. Data acquisition can be controlled by any suitable customized software program, such as the program developed by SEQUENOM® and discussed in 3.4. The instrument parameters are usually set on the local mass spectrometer using the instrument control software provided. These parameters are usually the same as those used for analysis of oligonucleotides with a typical dried-droplet sample preparation using 3-HPA matrix. Typically, parameters used on the Bruker Biflex III TOF-MS (linear mode) are: accelerating voltage of +20 kV, P2 lens, +18.9 kV, focusing lens voltage of 9.4 kV, and long delay >600 ns. The Biflex III is equipped with a LeCroy Waverunner digitizer; 6000 spectral points are acquired with sample bin set at 5 ns. The bandwidth-limiting filter (BWL) is on, corresponding to an input bandwidth of ~250 MHz in order to provide hardware smoothing of the mass spectra. The detector is gated so that ions below mass 2500 do not saturate the detector. The focal position of the nitrogen laser is adjusted to the surface of the sample. For high throughput analysis, a 20 Hz or faster laser and a high speed XY-table (e.g., 25 mm/sec top speed) are necessary. The reliability and reproducibility of the XY-table is essential.

3.5. Interactive Data Acquisition

The data acquisition and analysis unit, the SPECTRO-TYPER system (SEQUENOM, Inc., San Diego, Calif.), is a MALDI-based genotyping system that executes in real-time the signal processing and genotyping algorithms first used in its predecessor, the SPECTROTYPER system. The SPECTROTYPER system uses biology-based results to control data acquisition in the mass spectrometer, thereby significantly improving call efficiency and increasing the instrument throughput. Methods for real-time signal processing and genotyping to control data aquisition are known in the art, as exemplified in U.S. Pat. Pub. No. 20030033091.

Commercial MALDI mass spectrometers for use herein typically are capable of performing automated measurements on a series of samples. Standard software packages that enable automation also are available to those of skill in the art and include integrated algorithms that are used to judge the quality of the spectra. Such algorithms assess parameters such as the signal-to-noise ratio, peak resolution, and/or signal intensity within a specified mass range. If an acquired spectrum is determined to be of low quality, the instrument parameters may be adjusted and/or the stage may be moved ("rastered") to another section of the sample for re-acquisition of the spectrum. The cycle of evaluation and re-acquisition is repeated until either a spectrum of sufficient quality is acquired or a pre-specified number of acquisition attempts have been made. The spectrum is then saved and the system moves on to the next sample. In these systems, the integrated judging algorithms make their determination based on qualities of the spectra that are independent of the underlying assay or biological information contained in the spectra. During an automated run, a spectrum for each sample is stored. Then special purpose algorithms are employed that automatically determine the sample genotype. SPECTROTYPER is one of the available automated data processing system that determines one or more genotypes in each sample, depending on the assay definition for that sample, and assigns each a quality that is, from best to worst, —conservative, moderate, aggressive, low probability, or bad spectrum.

In the system described above, a combination of automated data collection routines and automated data processing routines, two different sets of criteria are used to judge the spectra; one set of criteria is used to control the data acquisition process, and a separate set is used to determine the biological significance of the acquired spectrum. Using such two-step acquisition and analysis routines may result in missed calls and unnecessarily long acquisition times. This is because the spectral features that define a clean acquisition are not necessarily the same features required for accurate genotyping. For example, the presence of large primer peaks due to incomplete extension may render a spectrum acceptable in terms of signal to noise criteria in a predefined mass window, but the resulting spectrum might not be of sufficient quality to allow determination of an unambiguous genotype. It is also possible that a spectrum that is of high quality for genotyping has a signal-to-noise ratio that causes repeated sampling by the data collection algorithm. In this case, unneeded data would be collected with a corresponding decrease in throughput. When different criteria are used for data collection and for data analysis it will always be possible that either the data collected does not give a suitable biological result or that extra data is collected resulting in lower throughput. Furthermore, the mismatches between the two judging methods become more common as the spectra from a sample become more complex, as with highly multiplexed samples. Integration of the data analysis and data collection algorithms should therefore result in faster, more accurate MALDI genotyping. A potential problem with a system that runs biology-based signal processing in real-time is throughput. The assay-based algorithms can take a significant amount of time to run. In order to have acceptable performance and actually realize the possible throughput advantages from biology-based instrument control, it is necessary to optimize the algorithms and to optimize the hardware platform on which the algorithms run.

Another one of the systems available is SPECTROTYPER system, which is a modification of the SPECTROTYPER system that includes highly optimized versions of the calling algorithms with a streamlined interface to a database to store the genotyping results. As part of the optimization, a well-defined programming interface was developed that controls the dialog between the data acquisition component and the biological-calling component of spectra analysis. The interface is flexible and modular to allow modification of the calling algorithms.

The following examples are included for illustrative purposes only and are not intended to limit the scope of the invention.

Example 1

Optimizing PCR Amplification Conditions and Homogeneous Mass Primer Extension Conditions The methods provided herein optimize the highest levels of multiplexing using generic biology conditions still suitable for MALDI-TOF mass spectrometry analysis of primer mass extension genotyping primers from a homogeneous primer mass extension reaction. For this method of optimization, a multiplexing level of 12-plex was selected to optimize the most robust conditions for high level multiplexing.

For each of the optimization experiments conducted in Example 1 herein, the PCR primers did not have sequence tags attached thereto. The addition of sequence tags as set forth in Examples 2 and 3 further enhanced the optimized conditions achieved for PCR primers not having sequence tags.

Experimental Setup:

A reference set of SNPs assays composed of 1000 individual SNP assays were used for our optimization procedures. From these 1000 assays, the MASSARRAY® Assay Designer software version 1.6 combined successfully seven 12-plexes, totaling 84 assays. The seven 12-plex reactions were analyzed by row in 7 DNA samples and 1 negative control in triplicate (168 12-plex reactions for 2 PCR conditions). One row was used for each of the seven 12-plex reactions comparing the commercial product conditions and the PCR A or PCR B conditions in the same 384 MTP.

Experimental Procedures:

The conditions described here as "Commercial Product", refer to the protocol for multiplexing hME as described in the MASSARRAY® user guide Version 1 Revision 6, which is incorporated herein by reference in its entirety. The PCR A and PCR B conditions are modifications of the commercial product conditions as described below.

Primer extension primers adjustment: The quality of the oligonucleotide primers used for the primer mass extension hME assays were tested as described in the Multiplex Mass Extension Primer Concentration Adjustment section of Example 2. Because the peaks in the mass spectrum for a multiplexing reaction may not have comparable heights. Variations in peak height may stem from incorrect concentrations or different unpredictable desorption/ionization behavior in MALDI. The hME primers mixtures were evaluated by MALDI-TOF at a final concentration of 360 nM each. Following spectra analysis, the mixes were corrected using the guidelines provided herein. Results confirmed the benefits of performing this correction in high level multiplexing.

Exo/Sap dephosphorylation conditions: In these Example 1 experiments where sequence tags were not attached to the PCR primers, when Exonuclease 1 was used, the incubation parameters were different from the SAP only post-PCR treatment procedure: 20 min. at 37° C., 15 min. at 85° C., and then stored at 4° C. The longer deactivation time was used in order to completely deactivate the exonuclease 1 enzyme.

hME conditions tested: Following preliminary experiments, it was found that an increase in the concentration of nucleotides, Thermosequenase enzyme, and extend primers appeared to have the most significant effects on increasing the calling rate and on the overall molecular biology of the system. Also, in these Example 1 experiments where sequence tags were not attached to the PCR primers, the addition of 0.3 Units of Exonuclease 1 to the SAP treatment appeared to increase robustness. Also, the addition of extra pyrophosphatase was tested in order to degrade excess of pyrophosphates from the multiplex PCR products. No significant improvement was observed by adding up to 0.2 Units of pyrophosphatase. Table 3 below shows the two main hME conditions that were used in this study. For these particular Example 1 optimization assays where no sequence tags were attached to the PCR primers, it was found that the use of Exonuclease 1 with SAP in the dNTP dephosphorylation step optimized and increased the overall call rate for hME assays (no sequence tags). The use of Exonuclease 1 in this step for hME assays where sequence tags were attached to the PCR primers did not have a beneficial impact on the overall reaction. Thus, the use of Exonuclease 1 is not necessary in the multiplexed methods set forth in Examples 2 and 3, where sequence tags are attached to the PCR primers.

TABLE 3

Post PCR chemistry.

|  | Commercial Product | hME A | hME B |
|---|---|---|---|
| Exo/SAP (2 μl) |  |  |  |
| THERMOSEQUENASE ™ buffer | 1X | 1X | 1X |
| SAP | 0.3 U | 0.3 U | 0.3 U |
| Exo1 |  | 0.3 U | 0.3 U |
| HME (2 μl) |  |  |  |
| THERMOSEQUENASE ™ buffer | 1X | 1X | 1X |
| d/ddNTP Mix | 50 μM | 100 μM | 100 μM |
| THERMOSEQUENASE ™ | 0.576 U | 0.576 U | 1.5 U |
| HME probes | 0.6 μM | 1 μM | 1 μM |

Comparison of the hME A and hME B reactive components used in this study with the commercial product conditions, when sequence tags are not attached to the PCR primers.

Optimization Strategy:

Following preliminary experiments, a list of variables for optimization was established and other variables were kept fixed for the current study (see Table 4). The optimization was done in two stages: First, the PCR was optimized and then the impact of the optimized PCR conditions on the hME assay was assessed. During the second stage, three different hME reaction conditions were assessed along with different cycle conditions.

TABLE 4

Variables in hME

| Significant Variables Identified | Fixed Variables |
|---|---|
| PCR reagents and buffer | Assay Design (Designer 2.0) |
| Pre-Extend reagents and buffer | PCR cycling conditions |
| Extend reagents and buffer | Oligonucleotides Quality |
| Extend cycling conditions | Acquisition and Analysis (Typer-RT, 3.0.1.14) |
| Desalting conditions | Dispensing using the Mol. Bio. Pintool |
| MALDI parameters sets | Measurement using the Mol. Bio. biflex |
|  | Liquid handling (MP11 Packard, Hamilton) |

1) PCR Optimization:

Sets of multiplex PCR reaction conditions were established using the Taguchi method (*Nucl. Acids Res.* 1994, 3801-3805). The PCR A conditions were compared with the commercial product PCR conditions (see e.g., Table 5). The PCR condition A (PCR A) produced 1.6 to 3.6 fold more amplification products with an average of 2.1+/−0.4 over 7 different 12-plex reactions compared to the Commercial Product PCR conditions. Subsequent hME analyses comparing the PCR A conditions to the Commercial Product PCR conditions demonstrated that the PCR A conditions performed worse in terms of the number of calls made (e.g., the calling rate also referred to herein as the "% of the attempted genotypes determined"). It was thought that the use of an excess amount of salts (e.g., excess initial $MgCl_2$, or excess "free Mg2+") might be inhibiting thermosequenase enzyme activity. In addition, it was thought that an excess amount of salt might be overwhelming the desalting step. Therefore, the PCR buffer concentration was titrated down and a compromise concentration of $MgCl_2$ was identified corresponding to 1.25× of the HOTSTARTAQ® PCR 10× Buffer. The identified titrated PCR conditions are referred to as "PCR B" in Table 5.

The "Commercial Product" PCR conditions contained 2.5 mM $MgCl_2$ final concentration (1× of HOTSTARTAQ® PCR 10× Buffer containing 15 mM $MgCl_2$+1.0 mM $MgCl_2$ added); the PCR A conditions contained 4.625 mM $MgCl_2$ final concentration (2× of HOTSTARTAQ® PCR 10× Buffer containing 15 mM $MgCl_2$+1.625 mM $MgCl_2$ added); and the "PCR B" PCR conditions contained 3.5 mM $MgCl_2$ final concentration (1.25× of HOTSTARTAQ® PCR 10× Buffer containing 15 mM $MgCl_2$+1.625 mM $MgCl_2$ added). As set forth in Table 5, the "free Mg2+" for each of the PCR reaction conditions can be calculated. For the Commercial Product conditions, the free Mg2+=1.7 mM; for PCR A conditions free Mg2+=2.265 mM; for PCR B conditions free Mg2+=1.5 mM. It was found that the PCR B conditions provided PCR amplification rates comparable to the PCR A conditions. Following preliminary experiments, it was decided to keep the PCR cycling conditions fixed as described in the manual.

TABLE 5

PCR conditions comparison.

|  | Control | PCR A | PCR B |
|---|---|---|---|
| Genomic DNA (ng/rxt) | 2.5 | 2 | 2 |
| *HOTSTARTAQ ® PCR Buffer | 1X | 2X | 1.25X |
| dNTPs (μM) | 200 | 500 | 500 |
| MgCl2 (mM) | 2.5 | 4.625 | 3.5 |
| PCR Primers (nM) | 50 | 100 | 100 |
| HOTSTARTAQ ® (U/rxt) | 0.1 | 0.15 | 0.15 |

The fixed conditions: 5 μl reactions volume in 384 well MTP.
Standard cycling conditions: 94° C. 15', 94° C. 20", 56° C. 30", 72° C. 1' for 45 cycles, 72° C. 3'.
Liquid handling: combination of Packard and the Hamilton instruments.

2) hME Optimization:

Uniplexing statistics: In order to evaluate the multiplexing reactions, the 84 assays were first tested in uniplexing mode. Seven DNA samples and one negative control were analyzed in triplicate. Three assays consistently failed giving a design and implementation rate of 96.4%. Following gel analysis, those failures were found to occur at the PCR level. 1679 out of 1704 of the remaining reactions worked giving an analytical efficiency of 98.5%. Overall, a success rate of 95.2% was obtained, which complies with previous uniplexing studies. Only two calls out of 1764 were inconsistent with the two other determinations (including one aggressive call). This suggests a calling accuracy of 99.95%. We calculated an average hME primer extension of 73.3%±4 (mean of 7 groups). We also found an average pausing rate of 6.3%±1. Those results set the maximum possible standards for multiplexing.

Multiplexing optimization: The commercial product hME conditions as described in Table 3 were initially used for multiplexing. An average calling rate of 35%±5 was obtained, which means that only four combined PCR amplification and primer mass extension assays out of 12 worked using the standard protocol. When 20 cycles were added during the primer extension step, the calling rate raised to 50.9%±4. This result suggested that the extension step was limiting in the commercial product conditions. Also, as described in the previous section, PCR condition A was giving optimal PCR amplification. This condition seemed to have inhibitory effects on the thermosequenase activity as well as potential effects on the matrix/analyte crystallization quality and overall MALDI efficiency leading to the observed reduction in calling rate.

As described the PCR conditions were re-optimized by titrating down the buffer concentration (PCR B, Table 5). Using the standard hME conditions in combination with the PCR B conditions, the calling rate was increased to 54.7%±7.8. From this point forward in these methods of optimization, the PCR conditions were fixed to "B PCR" set forth in Table 5. The addition of Exonuclease1, in this Example 1 reaction without sequence tags attached to the PCR primer, did not increase the calling rate significantly but appeared to reduce deviation and therefore appeared to improve robustness (0.05 percent/assay). The calling rate increased by 12% when 20 cycles were added at the primer extension step (66%). A further 3% improvement was obtained when the hME A conditions were used with 75 cycles. The hME B conditions performed best with a 77%±2 calling rate (>9/12). This combination of PCR B (see Table 5) and hME B (see Table 3) conditions also showed greater robustness as the experiment was repeated and produced rates within a low standard deviation. A minimum of 9 calls were made over 7 different 12-plex reactions using the herein developed generic protocol.

Because the addition of 20 thermocycles in the primer mass extension reaction significantly increased the yields of calls obtained (e.g., genotypes determined), this effect was investigated further. Plates were run and assayed using 55, 75 and 100 thermocycles during the primer mass extension reaction. The results showed positive correlations with both calling and primer extension rates. The use of the 100 cycles primer mass extension protocol did show little improvement when compared to the 75 cycles conditions suggesting that the plateau may lie between 75 and 100 thermocycles. Also using the reaction conditions provided herein, the primer extension rate became similar to the value found from the uniplexing data.

The multiplexing calling accuracy was assessed following comparison with the uniplexing data. The commercial product conditions produced 3% inaccuracy. The use of the PCR B conditions reduced inaccuracy to around 2% and in the combination with the hME conditions provided herein stabilized the miscalls rate at around 1 to 2%. Following extensive data analysis, it was found that over 90% of the calling errors were due to the inability to detect the second allele peak of heterozygous samples. This appeared to be restricted to a few select assays (~5) that have a tendency to discriminate amplification of the second allele (skewed amplification). For those assays, the Typer-RT has two options: 1) make a no call or 2) make an erroneous homozygous call. Often, the second peak is present but weak. In some cases the MASSARRAY Typer system does not see it as a true peak and therefore instead of making a low probability call (no call), makes a conservative wrong homozygous call. It has been found that these assays are skewed in uniplexing but are called correctly. Thus, this effect is enhanced in multiplexing, but the effect is not limited to multiplexing. In addition, it has been found that the overall spectra quality is lower in multiplexing, which reduces the detectability of the second allele peak.

It appears that the miscalls do not occur randomly, because only a few of the assays are unstable and problematic. For example, 12-flex reactions #3, #4 and #6 generated 100% accurate calls under the assay conditions provided herein. Whereas, all of the miscalls combined from the seven 12-plex assays (19) were generated by only 6 unstable assays. For example, all of the miscalls for 12-plex #1, #2 and #5 originated from a single assay within the respective 12-plex assay. In 12-plex #7, 9 out of 11 miscalls originated from a single assay.

A follow-up experiment was conducted that removed the weakest and most problematic assays from the seven 12-plex assays, by creating seven 9-plex reactions from the previous 12-plexes. The results indicate that it is possible to increase the calling rate by removing the weak assays. Most importantly, the miscalls decreased significantly using the conditions provided herein. These results provide further evidence that most of the miscalls in the 12-plex assays were generated by a select group of unstable assays, and not by the multiplexing reactions per se.

To confirm this hypothesis and to test the replex function of Designer 2.0, the same seven 12-plex assays were randomly replexed with a plexing limit set to 9 (these randomly replexed 9-plex assays are referred to as 9X-B). The calling and miscalls rates obtained were similar to those in the original 12-plex format. This result can be explained by the fact that the problematic assays were not excluded. Thus, it is believed that multiplexing is mainly limited by the assay design. The fact that the miscalls are not random can be advantageous.

Conclusions Regarding the Example 1 Assays where No Sequence Tags were Attached to the PCR Primers:

In general, multiplexing is more susceptible to variations affecting quality of reagents and hardware. The quality of the Chips, Matrix formulation, MALDI-TOF parameters settings, ion exchange resin, enzymes and reagents are important factors for a successful multiplexing analysis.

Using the optimization methods described herein, the following parameters in the overall homogeneous primer mass extension assay (FIG. 1) have been optimized: 1) Generic PCR conditions with a buffer composition still suitable for subsequent Thermosequenase activity in a primer mass extension reaction and for MALDI-TOF mass spectrometry analysis. 2) Generic hME buffer and cycling conditions and 3) MALDI-TOF-MS parameters. These modifications led to an increase in minimum analytical efficiency from 4 out of 12, up to 9 out of 12 successful assays in 12-plex reactions. When 9-plex reactions were tested by removing the 3 weakest and most problematic assays from the 12-plex reactions, the calling rate increased to 90% and the miscalls were completely eliminated using the conditions provided herein in one experiment. In 12-plex settings, it was found that most of the miscalls were due to allele skewing of select assays.

Example 2

Materials

For this particular example, the materials and protocols for SEQUENOM's hME reaction are listed. The hME assay is especially designed for SNP analysis. It is a single-tube reaction carried out in solution and requires only addition steps throughout the whole procedure. Therefore it is easily compatible with automated liquid handling. For the multiplex methods of genotyping a plurality of polymorphic loci provided herein, an optimized hME reaction follows an optimized genomic PCR amplification procedure, and in this particular embodiment, has been designed for an automated processing platform using SEQUENOM's MASSARRAY system. Although both hardware and software available from SEQUENOM are set forth in this particular exemplified embodiment, those of skill in the art will recognize that the optimized PCR and primer mass extension conditions provided in the methods herein can be used with other combinations of hardware and software packages known to those of skill in the art for mass spectrometry analysis.

Instruments
MASSARRAY® liquid handler
(SEQUENOM® catalog #11230)
SEQUENOM®
MASSARRAY® nanodispenser
(SEQUENOM® catalog #11153)
MASSARRAY® analyzer
(SEQUENOM® catalog #00450)
Software
MASSARRAY® Typer system version 2.0 or higher
(SEQUENOM® catalog #11406)
PROXSNP and PREXEND
(available, for example, through SEQUENOM's REALSNP.COM website and database)
Materials Common to PCR and hME
The following instruments or components are used to design and process PCR and hME reactions:
1. SPECTRODESIGNER software for assay design for PCR and hME reactions (SEQUENOM, Inc., San Diego, Calif.).
2. Multimek™ 96 Automated 96-channel pipettor (BECKMAN COULTER, Inc., Fullerton, Calif.; also available through SEQUENOM® as SPECTROPREP). Used with 20 μL tips, also from BECKMAN COULTER, Inc., Cat. no. 717254.
3. Thermal Cycler: either GENEAMP® PCR System 9700 (APPLIED BIOSYSTEMS®, Foster City, Calif.); or PTC-225 DNA ENGINE TETRAD® Cycler (MJ RESEARCH, Inc., Watertown, Mass.).
4. Rotator capable of holding microplates (e.g., FISHER SCIENTIFIC, Pittsburgh, Pa.; model 346).
5. SPECTROPOINT (pintool instrument for nanoliter dispensing onto a SPECTROCHIP®) or SPECTROJET (piezoelectric nanoliter dispenser); both are available through SEQUENOM®.
6. MALDI-TOF MS instruments: either BIFLEX® III (BRUKER, Bremen, Germany); or VOYAGER DE (APPLIED BIOSYSTEMS®, Foster City, Calif.). The instruments are used in connection with the SEQUENOM® SPECTROTYPER- and SPECTROTYPER RT software for data acquisition, automated processing, genotype analysis, and data storage. MS instruments are also available through SEQUENOM® with the appropriate software.
PCR-Specific Materials
1. 384-well microplates (MARSH BIOMEDICAL PRODUCTS, Inc., Rochester, N.Y., Cat. no. TF-0384).
2. High-performance liquid chromatography (HPLC) grade water.
3. Forward and reverse PCR primers (i.e., primary and secondary primer paris): 30 mers, desalted, resuspended in water and stored at −20° C.; e.g., from either INTEGRATED DNA TECHNOLOGIES, Inc. (Coralville, Iowa); or OPERON TECHNOLOGIES, Inc. (Alameda, Calif.).
4. Ultrapure dNTP set (AMERSHAM PHARMACIA BIOTECH, Inc., Piscataway, N.J.; stored at −20° C.).
5. HOTSTARTAQ® DNA Polymerase and buffer (QIAGEN, Inc., Valencia, Calif.; stored at −20° C.).
6. 25 mM MgCl$_2$ (comes with HOTSTARTAQ® DNA Polymerase).
7. Genomic DNA (2.5 ng/μL; stored at 4° C.).
hME-Specific Materials
1. Autoclaved type I water (resistance >18.2 MΩ/cm).
2. Shrimp Alkaline Phosphatase (SEQUENOM®; stored at −20° C.).
3. Primer mass extension primers (~20-mers, desalted, resuspended in water and stored at −20° C.; e.g., from either INTEGRATED DNA TECHNOLOGIES or OPERON TECHNOLOGIES).).
4. THERMO SEQUENASE™ DNA Polymerase and buffer (AMERSHAM PHARMACIA BIOTECH; also available through SEQUENOM®; stored at −20° C.).
5. 10× ddNTP/dNTP Termination mixes (premixed and ready-to-use from SEQUENOM® or as single components from AMERSHAM PHARMACIA BIOTECH; stored at −20° C.).
6. SPECTROCLEAN resin for sample desalting prior to mass spectrometry (SEQUENOM®; stored at room temperature [RT]).
7. 384-element silicon chip (SPECTROCHIP® from SEQUENOM®, used as platform for MALDI-TOF MS analysis, stored at RT in desiccated environment).
Primer Mass Extension Starter Kit
(SEQUENOM® catalog #10030)
Homogeneous Primer Mass Extension Mix
(SEQUENOM® catalog #10035-10051)
THERMO SEQUENASE™
(SEQUENOM® catalog #10052; also available from AMERSHAM BIOSCIENCES)
CLEAN RESIN
(SEQUENOM® catalog #10053)
Clean Kit
(SEQUENOM® catalog #11220)
Shrimp Alkaline Phosphatase (SAP)
(SEQUENOM® catalog #10002)
SPECTROCHIP®
384-well SPECTROCHIP®
(SEQUENOM® catalog #00601)

A. Assay Design

Seven 12-plex reactions were designed using the 30/20 strategy set forth herein. The reactions were processed following the procedure described below. Seven individual DNA samples and one negative control were analyzed in 6 replicates (36 reactions, 4032 assays). To design the high-level, multiplexed hME reactions provided herein, the MASSARRAY® Assay Design system (Assay Design) version 2.0 (commercially available from Sequenom, Inc., San Diego, Calif.) was used. This version uses a multiplexing strategy developed to take full advantage of the platform with minimal chances for overlapping peaks. The program is also designed to consider potential unwanted self and primer-primer interactions in order to avoid non-template extensions. Those of skill in the art will recognize that other mass spectrometry assay design programs can be used with the optimized PCR amplification and primer mass extension conditions provided herein, so long as such programs minimize overlapping peaks and unwanted self and primer-primer interactions in order to avoid non-template extensions.

A "30/20" strategy was used for optimal performance in combining the assays. As used herein, the term "30/20" refers to the Unknown (+/− of analytes) and the Min Separation (Da) settings on the By-product Contaminants dialog box and the main MASSARRAY® Assay Design window, respectively. Accordingly, "30" is entered in the By-product Contaminants dialog box and "20" is entered into the main MASSARRAY® Assay Design window. Additional information regarding the MASSARRAY® Assay Design system version 2.0 can be found in the MASSARRAY® *Design User's Guide*, version 2.0 (Sequenom, Inc. San Diego).

Primer Selection

Oligonucleotide sequences and Reference SNP IDs for one of the seven 12-plex reactions (12-plex #7) are described in Table 6 below (SEQ ID NOS 1-36, respectively, in order of appearance). The criteria for the selection of SNPs was based on minor allele frequency of at least 20% and availability of at least 400 bp of flanking sequences.

TABLE 6

Reference SNP IDs and oligonucleotide sequences for 12-plex #7 (the terminator mix used was ACT: ddATP; ddCTP; ddTTP; and dGTP)

| SNP ID | 2nd PCR Primer | 1st PCR Primer | AMP (bp) | Primer Mass Extension Primer |
|---|---|---|---|---|
| 170447 | ACGTTGGATGAAGACCACCACCCTCTCCATG (SEQ ID NO: 1) | ACGTTGGATGGCTGAGATGGTGTTAAAGGG (SEQ ID NO: 2) | 109 | CTCACGCCCCTGCCACC (SEQ ID NO: 3) |
| 108843 | ACGTTGGATGAATCACATGGCATCAACACC (SEQ ID NO: 4) | ACGTTGGATGTACAGTAACCTAGATTAGGC (SEQ ID NO: 5) | 94 | GCATCAACACCCGCCGC (SEQ ID NO: 6) |
| 35856 | ACGTTGGATGACTGCTGAAGCAGCCACGAC (SEQ ID NO: 7) | ACQTTGGATGAGCCTCTTGCCTACAGTGTC (SEQ ID NO: 8) | 96 | CCAGGGCAGGCTCTTCT (SEQ ID NO: 9) |
| 39524 | ACGTTGGATGTGGTATCTTCGGAAGACACG (SEQ ID NO: 10) | ACGTTGGATGACAATGTTGGATGCAAACGG (SEQ ID NO: 11) | 100 | GTTTTGACAGTGATGCA (SEQ ID NO: 12) |
| 33234 | ACGTTGGATGGAAAGGTCAAATACAGCCTC (SEQ ID NO: 13) | ACGTTGGATGCAGCTTTCAGCTGGAGGAAC (SEQ ID NO: 14) | 100 | AATACAGCCTCTTGCTTC (SEQ ID NO: 15) |
| 174529 | ACGTTGGATGTGAAATGGCTCAGCCTGTAG (SEQ ID NO: 16) | ACGTTGGATGCCCTCCATTTCTGAGGCAGG (SEQ ID NO: 17) | 97 | CTGGTGTGCCACCCAGGGC (SEQ ID NO: 18) |
| 90951 | ACGTTGGATGACACAGATGATGACCAGCAG (SEQ ID NO: 19) | ACGTTGGATGTTCCTCTCCAGTCCCTCCTG (SEQ ID NO: 20) | 117 | AGATGGCAGGGCCCAGAGC (SEQ ID NO: 21) |
| 174680 | ACGTTGGATGCATTTGGCGGCATGCTGAAG (SEQ ID NO: 22) | ACGTTGGATGCCTTCAAAAGTACCAAGGCC (SEQ ID NO: 23) | 104 | CTAGGAAGAGCTAGAGGCAA (SEQ ID NO: 24) |
| 193915 | ACGTTGGATGTGGCTGCTCCCTGATCCTAA (SEQ ID NO: 25) | ACGTTGGATGCATAGCCATCTTGGATACCC (SEQ ID NO: 26) | 96 | CTCCCTGATCCTAACTTCTGA (SEQ ID NO: 27) |
| 201422 | ACGTTGGATGTAGAATGCTACAACCACCGG (SEQ ID NO: 28) | ACGTTGGATGGTCCCTAATTCAAAGGTCCC (SEQ ID NO: 29) | 109 | TTTGTCATTAATTGGCCTACA (SEQ ID NO: 30) |
| 171012 | ACGTTGGATGGAATTCTTAGATCCAGCCAC (SEQ ID NO: 31) | ACGTTGGATGATGGTCACAGCATACAGCTC (SEQ ID NO: 32) | 112 | AGTCAATGTTTTTGACACAAGT (SEQ ID NO: 33) |
| 180870 | ACGTTGGATGACTGACAGAGATTCCTTGGC (SEQ ID NO: 34) | ACGTTGGATGACATTTCTAGAGAAACAGGC (SEQ ID NO: 35) | 106 | TTATTAYATCTTACACCCAAATGA (SEQ ID NO: 36) |

Note: Boldfaced portions of PCR primers is the hME-10tag

Polymerase Chain Reaction (PCR) Amplification:

Prior to conducting the homogenous primer mass extension genotyping reaction, the genomic DNA was amplified using an optimized polymerase chain reaction (PCR). It has been found that the use of a 10 mer tag, "hME-10" (5'-ACGTTGGATG-gene-specific-sequence-3') (10-mer shown in SEQ ID NO: 37), on the 5' ends of the PCR primers provides significant improvement in overall hME performance. In addition, the PCR cocktail composition was optimized to make multiplexing more robust.

To prepare and process the PCR amplification reaction, seven individual genomic DNAs were isolated from 10 mL of buffy coat samples using the PUREGENE® kit (GENTRA® Systems). The genomic DNA samples were purchased from the San Bernardino, Calif. blood bank. Race ethnicity and sex are unknown. The seven samples of genomic DNA were prepared at a concentration of 2.0-2.5 ng/µl in 0.25×TE (Tris-HCl buffered EDTA).

A optimized PCR reaction mix was assembled with the final concentration of reagents as shown in Table 7. The final concentration of $MgCl_2$ was 3.5 mM (HOTSTAR buffer plus the additional $MgCl_2$ added). The reaction was designed to amplify the regions encompassed by the PCR primer pairs set forth in Table 6.

TABLE 7

Optimized PCR Cocktail for Multiplexing

| Reagent | Volume | Final Concentration |
|---|---|---|
| Nanopure water | 0.920 µL | NA |
| Genomic DNA (2 ng/µL) | 1.000 µL | 2 ng/rxn |
| HOTSTARTAQ ® PCR buffer* containing 15 mM $MgCl_2$(10X) | 0.625 µL | 1.25x/ 1.875 mM $MgCl_2$ |
| Fresh dNTPs (25 mM)** | 0.100 µL | 500 µM each |
| Forward PCR primers*** (500 nM each) | 1.000 µL | 100 nM each |
| Reverse PCR primers*** (500 nM each) | 1.000 µL | 100 nM each |
| $MgCl_2$ (25 mM) | 0.325 µL | 3.5 mM/ 1.625 mM $MgCl_2$ added |
| HOTSTARTAQ ® (5 U/L) QIAGEN Inc. | 0.030 µL | 0.15 U/rxn |
| Total | 5.000 µL | |

*The PCR buffer concentration should not exceed 1.25X. Higher salt concentrations have negative effects at the hME level.
**Maximum of 5 freeze/thaws
***Containing a 10-mer tag: hME-10 (5'-ACGTTGGATG . . . ) (SEQ ID NO: 37).
NOTE:
Do not use the Q-SOLUTION. It has negative effects on MALDI-TOF-MS analysis.

The PCR reaction was thermocycled under the following conditions in a standard thermal cycler.

| 95° C. | 15 min |
|---|---|
| Forty-five cycles of: | |
| 95° C. | 20 sec |
| 56° C. | 30 sec |
| 72° C. | 1 min |
| Followed by: | |
| 72° C. | 3 min |
| 4° C. | hold |

The end results of the hME reaction in Example 2 indicate that all 12 nucleic acid target-regions were successfully amplified. The amplified nucleic acid target-regions were kept at 4° C. until further use.

hME Reaction

A. SAP Treatment to Neutralize Unincorporated dNTPs:

From the amplification reactions above, the remaining dNTPs from the PCR reaction were dephosphorylated (deactivated) to ensure that dNTPs will not be incorporated during subsequent transcription using R&DNA Polymerase. The SAP enzyme was used to dephosphorylate unincorporated dNTPs from the amplification reaction as follows.

A master mix of 1.53 µl nanopure water, 0.17 µl hME buffer (10×; 260 mM Tris-Hcl pH 9.5, and 6 mM MgCl$_2$ and 0.3 µl of shrimp alkaline phosphatase (SAP; 1 U/µl; AMERSHAM PHARMACIA; Piscataway, N.J.) was prepared per sample. For a 384 well plate, the master mix consisted of 881.3 µl nanopure water, 97.9 µl hME buffer and 172.8 µl SAP. The master mix was vortexed for five seconds to mix the solution and then 92 µl of the mix was pipetted into each well of the last horizontal row of a 96-well vee-bottom polystyrene microtiter plate (STARSTEDT Inc., Newton, N.C.). From each of these wells, 2 µl of solution was added to each PCR reaction in a 384-well microtiter plate (from Example 2), which produced a final volume of 7 µl. The microtiter plate was sealed with Microseal A (ABGENE®; Rochester, N.Y.) and then subjected to a cycle at 37° C. for 20 minutes, followed by 85° C. for 5 minutes and stored at 4° C.

Multiplex Mass Extension Primer Concentration Adjustment:

In certain embodiments, the peaks in the mass spectrum for a multiplexed reaction may not have comparable heights. Variations in peak height may stem from 1) inconsistent oligonucleotide quality and 2) unpredictable desorption/ionization behavior in MALDI. To achieve the best multiplexing results, it is recommended that the concentrations of hME primers be adjusted to even out peak heights (intensities) in the mass spectrum. This adjustment must be done prior to preparing the hME reaction cocktail and processing the hME reaction set forth herein.

Adjusting primer mass extension primer mixes requires the use of a SPECTROCHIP®. Adjusting primer mass extension primer mixes is important for successful multiplexing. Without adjustment an assay with a very low primer peak will systematically fail when applied to samples as part of a multiplex.

To adjust primer mass extension primer mixes perform the following steps:

1. For each multiplex, prepare a mixture of the required primer mass extension primers (referred to as a primer mix). The final concentration of each primer in the primer mix must be 9 µM.

Consider how much primer mix is needed. Each single hME reaction (i.e., a single well in a 384-well microplate) requires 1 µL primer mix.

When obtaining primer mass extension primers, it may be useful to consider what plex-level will be used and obtain the primers at a certain concentration. For example, ordering primers for a 12-plex at 108 µM makes preparing primer mixes much easier. Equal volumes of each 108 µM primer can then be mixed. Each Primer will have a concentration of 9 µM in the final primer mix. Similarly, for a 10-plex, ordering primer mass extension primers at 90 µM allows preparation of primer mixes by simply mixing equal volumes.

2. Pipette 1 µL of the primer mix into a well in a microplate and then add 24 µL nanopure water to the well. The well now contains a 360 nM dilution of the primer mix (referred to as a primer mix sample).

3. Repeat steps 1 and 2 for each multiplex, pipetting each primer mix into a different well of the same microplate, until the microplate contains primer mix samples for all of the multiplexes.

4. Add 3 mg CLEAN RESIN (resin) to each well containing primer mix sample:

Follow the standard method of using the dimple plate to transfer resin to the microplate. If all wells of the microplate are not used, only fill the portion of the dimple plate corresponding to the wells in the microplate containing primer mix samples.

The standard protocol for adding resin calls for the addition of 16 µL nanopure water after adding resin to each well. Do not add any water. The primer mix samples already contain all necessary water.

5. Dispense the primer mix samples to a SPECTROCHIP® for the normal hME reaction products.

For instructions on operating the nanodispenser, see the "Dispensing primer mass extension Reaction Products onto SpectroCHiPs" chapter in MASSARRAY® *Nanodispenser User's Guide*.

6. Using MASSARRAY® Typer (Typer) system version 2.0 or higher, acquire spectra from the SPECTROCHIP® as usual.

Use the assay definitions (in Typer) for the actual multiplexes. Each well on the SPECTROCHIP® will yield no-calls because there is no analyte, only unextended primer mass extension primers. A peak should appear at the expected mass for each primer mass extension primer in the mix.

This point is a good opportunity to "quality-check" the primer mass extension primers and the primer mixes. There should be a peak at the expected mass of each primer. A missing peak generally indicates poor primer quality or a primer missing from the mix. An unexpected peak generally indicates poor primer quality or the addition of an unnecessary primer to the mix.

For instructions on acquiring spectra, see the "SPECTROACQUIRE" chapter in MASSARRAY® *Typer User's Guide*.

7. Check whether the primer peaks in each mass spectrum have comparable heights. If all peaks are at least 50% of the height of the highest peak, they are acceptable. If any peak is less than 50% of the height of the highest peak, add more of the primer having the short peak to the primer mix. Use the following general guidelines on bringing up the peak height of a primer, which are only rough, initial guidelines: If a peak for a primer is 40% the height of the highest peak in the spectrum, add 40% more of that primer to the primer mix; if a peak for a primer is 30% the height of the highest peak in the spectrum, add 60% more of that primer to the primer mix; and if a peak for a primer is 20% the height of the highest peak in the spectrum, add 80% more of that primer to the primer mix.

Once the concentrations of the primers have been adjusted in the primer mix to even out peak heights, use the adjusted primer mix in actual assay runs.

Adjust the original primer mix, not the primer mix sample in the microplate.

B. Multiplexed Primer Mass Extension (hME) Reaction:

The primer mass extension assay was designed to detect the nucleotides on the complementary strand at the respective polymorphic positions set forth in Table 6.

Table 8 provides the hME cocktail components and preparations for 12-plex multiplex reactions provided herein.

TABLE 8

Optimized hME reaction master mix cocktail for multiplexing

| Reagent | Volume | Final Concentration |
|---|---|---|
| Nanopure water | 0.76 μL | NA |
| Appropriate hME EXTEND Mix (containing buffer and d/ddNTPs) | 0.20 μL | 50 μM each d/ddNTP |
| Adjusted primer mass extension primer mix ~9 μM each primer, adjusted)* | 1.00 μL | ~1 μM each |
| THERMO SEQUENASE ™ (32 U/μL) | 0.04 μL | 1.25 U/rxn |

*The primer mass extension primer mix must have been adjusted, if necessary, as described in "Adjusting Primer Mass Extension Primer Mixes" herein. Note that the primers in an adjusted mix may not be at 9 μM each. Each starts out at 9 μM, however, the addition of extra amounts of some primers to adjust the concentration may not be exactly 1 μM.

A master mix for primer mass extension reactions was made as in Table 8, using Primer Mass Extension THERMO SEQUENASE™. The enzyme was kept at −20° C. until it was added to the mix. The template specific hME primers were as set forth in Table 6. The volume of the master mix included about 38% overhang (extra volume) to account for pipetting losses. 2 μl of the hME primer mass extension master mix was added to each well of the microtiter plate containing the SAP treated reactions (9 μl final volume). For the 12-Plex reaction #7 (PCR and genotyping primers set forth in Table 6) the termination mix used was ACT, which corresponds to ddATP, ddCTP, ddTTP and to dGTPs (e.g., 3 ddNTPs to 1 dNTP). The plate was sealed with Microseal "A" film (MJ RESEARCH Inc., S. San Francisco, Calif.).

The reactions were thermocycled as follows:

| 94° C. | 2 min |
|---|---|
| 75 cycles of: | |
| 94° C. | 5 sec |
| 52° C. | 5 sec |
| 72° C. | 5 sec |
| Followed by: | |
| 4° C. | hold |

For reactions with multiplexed primers, 100 cycles used in place of 75 cycles in the thermocycling has been found to improve the performance genotyping primer mass extension reactions.

C. Desalting of the hME Reactions:

16.0 μl of ddH2O was added to each sample within the 384 well plate. Using the SPECTROPREP (SEQUENOM®, San Diego Calif.), 3 mg of cation exchange resin (SPECTROCLEAN; SEQUENOM®; San Diego, Calif.) was added to each well and rotated for 5 min. The samples were spun down for 5 minutes at 640×g (2000 rpm, centrifuge IEC Centra CL3R, rotor CAT.244).

D. MALDI-TOF Analysis:

The samples were transferred onto a 384-well SPECTROCHIP® (SEQUENOM®; San Diego, Calif.) for MALDI-TOF analysis using a nanodispenser to robotically dispensing approximately 16 nl of each sample onto the SPECTROCHIP®. The entire SPECTROCHIP® microchip was transferred into a BRUKER/SEQUENOM® mass spectrometer, which allowed automated measurement of the samples. Positive ions were analyzed and ~100 single shot spectra were accumulated (e.g., 5 raster positions×20 shots/position). All samples were analyzed in linear time-of-flight mode using delayed ion extraction and a total acceleration voltage of 20 kV. See the "Dispensing Primer Mass Extension Reaction Products onto SPECTROCHIP®" chapter in MASSARRAY® *Nanodispenser User's Guide* available from SEQUENOM® (San Diego, Calif.) for instructions.

E. Acquiring Spectra (MALDI-TOF-MS)

The MASSARRAY® Typer system (Typer version 3.0) was used to acquire spectra from the SPECTROCHIP® as described in the "SPECTROACQUIRE" chapter in MASSARRAY® *Typer User's Guide* also available from SEQUENOM® (San Diego, Calif.).

Results

One thousand SNPs were selected and processed through Assay Design 2.0 and the EXTEND suite. The design parameters were set as depicted using the "30/20 strategy" set forth herein. Out of the 964 assays designed, 864 were combined into 12-plexes (90% plexing efficiency). The design results are shown in Table 9.

TABLE 9

Multiplexing hME assays (Design Results)

| Pass* | 1000 | 100% |
|---|---|---|
| Pass* | 997 | 99.7% |
| Assays designed | 964 | 96.4% |
| Assays 12-plexed | 864 | 86.4% |
| 12-Plex efficiency** | 72/80 (90%) | NA |

*PROXSNP and PREXTEND are part of the EXTEND suite of programs available, for example, through SEQUENOM's RealSNP.com ™ web site and to customers. PROXSNP checks SNP syntax, performs a BLAST genome search, and checks for other SNPs in the vicinity of the SNP in question-"pass" means the SNP is correctly formatted and a match was found in the genome. PREXTEND searches the genome for matches to the PCR primer-"pass" means the primers match the genome in only one location.
**This is a ratio of successfully designed 12-plexes to the number of 12-plexes numerically possible. In this case, out of 80 possible 12-plexes, 72 were successfully designed. (There are 80 12-plexes possible out of the 964 assays designed; 864 of those assays were successfully grouped into 72 12-plexes.)
† These percentages compare design results to the original 1000 assays that passed PROXSNP.

Those of skill in the art recognize that other known assay design programs can be used herein to design 12-plex multiplex reactions for use with the optimized methods provided herein.

Multiplexing Using Primer Mass Extension

Seven 12-plex reactions were designed using the 30/20 strategy provided herein. The seven 12-plex reactions were processed following the procedure described above for 12-plex #7. Seven individual DNA samples and one negative control were analyzed in 6 replicates (36 reactions, 4032 assays). The success rates (Calls %) ranged from 84% to 96%, and the reproducibility to genotyping data obtained from independent uniplexed hME reactions done in quadruplicate (Accuracy %) ranged from 98.7% to 100%. These are first pass results obtained using MASSARRAY® Typer system (version 3.01) commercially available from SEQUENOM® (San Diego, Calif.). These are averages of six replicates performed on seven previously genotyped genomic DNA samples. Calls: The average percentage of successful real-time calls are indicated by the left bar in each pair. Accuracy: The average percentage of accurate real-time calls are indicated by the right bar in each pair. Standard deviation is indicated at the top of each bar. As an example, the reference SNP IDs and oligonucleotide sequences for one of these 12-plexes (#7) are listed in Table 6.

Thus, multiplexed reaction performances are improved using the optimized conditions provided herein (e.g., PCR/hME conditions provided herein with hME-10 tags). Individual 12-plex success rates varied from 84 to 96% with accuracies from 98.7 to 100%. The overall average call rate and accuracy obtained (90 and 99.7%, respectively) are in agreement with a previous study conducted by the Whitehead Institute Center for Genome Research performed at lower plex-levels, which was an accuracy rate estimated to be 99.6%.

Viewing the results as a whole, the accuracy is estimated to be 99.7%. It is important to note that these are first-pass genotypes. Weak assays were not filtered out. Inaccuracies in a multiplex can be attributed to particular, individual assays. It is believed that if such assays were filtered out (as described in Example 1 for assays having PCR primers without sequence tags attached), the accuracy would improve. For instance, 12-plex #2 produced 6 errors. These errors were generated by only two problematic assays.

Performance variability between multiplexes is attributed to unpredictable behavior of individual assays when combined at higher plex-levels. Out of the 84 assays used in this study, 10 exhibited significantly weaker extension rates as compared to the uniplexing format. These assays provided lower calling rates and were more prone to generate errors. As described in Example 1 herein, it has been found that such assays with weaker extension rates do not behave randomly and, therefore, problematic assays can be detected and filtered out for further reactions/analysis.

Higher plex-levels generate spectra of higher complexity. The increased amounts of analytes in multiplexes may lead to lower signal-to-noise ratios because there is increased competition between the analytes. This effect can be at least partly alleviated by using higher concentrations of specific hME primers (see "Adjusting Primer Mass Extension Primer Mixes" described herein). In addition, for the best results, ensure that the hardware instrumentation used, such as MASSARRAY® instruments receive all routine maintenance and optimization. Note that the baseline in spectra may not appear perfectly flat. This is a normal characteristic of spectra for high-level multiplexes.

As set forth in Example 1, in addition to weak primer extension assays, errors can also stem from biased amplification of some SNPs—an effect observed in uniplexing and enhanced in high-level multiplexing. Coupled with high-mass assays, some heterozygous SNPs were called homozygous because a second allele peak was not detectable. Among the 4,032 genotypes obtained, 16 errors were attributable to only 8 assays. 12-plex #2 produced 6 errors generated by only two problematic assays (due to biased amplification). As set forth herein, because these errors are not random, problematic assays may be detectable and filtered out through cluster and Hardy-Weinberg equilibrium analyses.

Provided herein, is a generic protocol for performing high-level multiplexing of primer mass extension (hME). Using the optimized methods provided herein, it was possible to combine up to 12 assays together with over 90% success—both in the number successfully combined into 12-plexes and the number of genotypes determined (e.g., calls made by MASSARRAY® Typer system, first pass). These conditions were found to be the most robust, offering the best performance over the majority of assay combinations tested. The advantages obtained from the multiplexed methods of genotyping a plurality of polymorphic loci provided herein include higher throughput; lower cost per genotype; and higher accuracy. While 12-plex reactions were exemplified herein, the optimized PCR and primer mass extension reaction conditions provided herein are applicable to any multiplex-level up to 50-plex or more Example 3

As a comparison to the optimized methods provided herein, a 12-plex multiplex amplification and homogenous mass extension reaction was conducted using the previous PCR amplification conditions and the homogenous primer mass extension conditions set forth in the SPECTROPREP User's Guide version 1 Revision 6, dated May 29, 2002, which incorporated herein by reference in its entirety. Success and accuracy rates were compared using:

Previous experimental conditions (Old PCR-hME as described in MASSARRAY® *Liquid Handler User's Guide* v1 r6) without tags Experimental conditions provided herein (PCR-hME) without tags Conditions provided herein (PCR-hME) with tags (hME-10 tag)

Thus, three different reactions were compared: 1) the PCR amplification and homogeneous primer mass extension reactions set forth in Example 2 that included the hME-10 sequence tag on each PCR amplification primer; 2) the PCR amplification and homogeneous primer mass extension reactions set forth in Example 2, except that no sequence tags were included on any PCR amplification primer; and 3) the previous PCR amplification conditions and the homogenous primer mass extension conditions set forth in the SPECTROPREP-User's Guide version 1 Revision 6, dated May 29, 2002, that also did not contain any sequence tags attached to the PCR primers. The previous PCR amplification conditions were the same as those set forth in Example 2, except that final concentrations of: the dNTPs were 200 µM each; the Forward and Reverse primers were 50 nM each, the HOTSTARTAQ® polymerase was 0.1 U/rxn; the MgCl$_2$ was 2.5 mM; and the genomic DNA was 2.5 ng/rxn, as set forth in Table 10 below.

TABLE 10

Prior PCR Cocktail for Multiplexing

| Reagent | Volume | Final Concentration |
|---|---|---|
| Nanopure water | 2.240 µL | NA |
| Genomic DNA (2 ng/µL) | 1.000 µL | 2.5 ng/rxn |
| 10× HOTSTARTAQ ® PCR buffer containing 15 mM MgCl$_2$(QIAGEN ®) | 0.500 µL | 1X/ 1.5 mM MgCl$_2$ |
| Fresh dNTPs (25 mM) | 0.040 µL | 200 µM each |
| Forward and Reverse PCR primers (0.25 µM each) | 1.000 µL | 50 nM each |
| MgCl$_2$ (25 mM) | 0.20 µL | 1 mM added/ 2.5 mM final MgCl$_2$ |
| HOTSTARTAQ ® (5 U/L) QIAGEN Inc. | 0.020 µL | 0.10 U/rxn |
| Total | 5.000 µL | |

The previous hME conditions were the same as those set forth in Example 2, except that the primer mass extension primers were at a final concentration of 555 nM and the THERMO SEQUENASE™ enzyme was at a final concentration of 0.063 U/μl set forth in Table 11 below.

TABLE 11

Prior hME reaction master mix cocktail for multiplexing

| Reagent | Volume | Final Concentration |
| --- | --- | --- |
| Nanopure water | 1.282 μL | NA |
| Appropriate hME EXTEND Mix (containing buffer and d/ddNTPs) | 0.200 μL | 50 μM each d/ddNTP |
| Primer mass extension primers (10 μM each) | 0.500 μL | 555 nM each |
| THERMOSEQUENASE ™ (32 U/μL) | 0.018 μL | 0.58 U/rxn |

The results of seven 12-plex amplification reactions using the previous PCR amplification and primer mass extension conditions resulted in the amplification and extension of about 35% (en.g., at most 4 out of 12) of the nucleic acid target-regions. The average percentage of successful real-time calls are indicated by left bars (left bar in each pair). The average percentage of accurate real-time calls are indicated by right bars (right bar in each pair). Standard deviation is indicated at the top of each bar. Three experimental conditions were compared. The results show averages of seven 12-plex reactions (84 assays) performed on seven previously genotyped genomic DNA samples. The experiments were performed in 5 replicates. The experimental conditions used are indicated at the bottom of the chart. These are first pass results obtained by MASSARRAY® Typer system version 3.0.1. In this particular example, success and accuracy rates were defined by the average percentage of calls made in real-time by MASSARRAY® Typer system 3.0.1. Those of skill in the art can also obtain success and accuracy rates using other well-known mass spectrometry genotyping software systems or manually.

Accordingly, the 12-plex multiplexing efficiency of the previous amplification reaction conditions was about 35%, which resulted in an overall efficiency of genotyping calls made in the combined PCR amplification and homogenous primer mass extension genotyping reactions of no more than about 35%. The PCR amplification and hME primer mass extension conditions provided herein, without the use of Sequence tags on the PCR amplification primers, resulted in about 70% overall efficiency in both amplification and primer mass extension. Whereas the PCR amplification and hME primer mass extension conditions provided herein in Example 2, that included the use of sequence tags on the PCR amplification primers, resulted in at least about 90% overall efficiency in both amplification and primer mass extension.

Accuracy refers to reproducibility compared to previous genotype data obtained from independent, uniplexed, hME reactions done in quadruplicate. Using the optimized methods provided herein, results show that it is now possible to perform high-level multiplexing producing over 90% successful genotypes with 99.7% accuracy (automated MASSARRAY® Typer calls, first pass). Performances significantly dropped when the previous experimental conditions were used. Also the positive effects of using the hME-10 tag were demonstrated. Following real-time analysis, the genotypes can be validated by clustering signal-to-noise ratios and assays can be evaluated by Hardy-Weinberg equilibrium analyses. These type of "post-RT" analyses can be used to correct and/or reject genotypes, further improving overall accuracy.

Since modifications will be apparent to those of skill in the art, it is intended that this invention be limited by the scope of the appended claims.

What is claimed is:

1. A multiplex method of genotyping a plurality of polymorphic loci, comprising:
   (a) simultaneously amplifying a plurality of nucleic acid-target regions with amplification primer pairs under amplification conditions to produce an amplified mixture of nucleic acid-target regions containing polymorphic loci wherein the amplification conditions comprise dNTPs and for at least one amplification primer pair, one primer is in lower concentration than the other primer;
   (b) after (a) contacting the amplified mixture of nucleic acid-target regions with genotyping primers in the presence of at least one chain terminating reagent under primer mass extension conditions whereby the primers are extended up to, or through, the respective polymorphic loci, wherein there is one genotyping primer for each polymorphic locus and wherein the extension conditions comprise at least 55 thermal cycles;
   (c) determining the mass of the extended genotyping primers; and
   (d) determining the genotypes of the plurality of polymorphic loci from the mass of the extended genotyping primers.

2. The method of claim 1, wherein a sequence tag is attached to one or more primer pairs.

3. The method of claim 1, wherein only a single primer pair is utilized to amplify each particular nucleic acid-target region.

4. The method of claim 1, wherein the amplification-reaction conditions comprise water, genomic DNA, a buffer, dNTPs, the primer pairs, $MgCl_2$, and a polymerase, wherein the ratio of the concentration of $MgCl_2$ to the concentration of each one of the dNTPs is selected from $\leq 10:1$, $\leq 9:1$, $\leq 8:1$, $\leq 7:1$, $\leq 6:1$, or $\leq 5:1$.

5. The method of claim 4, wherein the polymerase is Taq polymerase at a concentration of 0.03 units/μl.

6. The method of claim 1, wherein the amplification-reaction conditions comprise between about 400-700 μM of each dNTP, about 100 nM primer pairs, and between about 2.6 up to about 4.8 mM $MgCl_2$.

7. The method of claim 1, wherein a sequence tag is attached to a primer in a primer pair.

8. The method of claim 1, wherein the extension conditions comprise at least 65 thermal cycles.

9. The method of claim 1, wherein the extension conditions comprise at least 100 thermal cycles.

10. The method of claim 1, wherein the concentration of each genotyping primer is selected to even out the mass intensities of the extended genotyping primers.

11. The method of claim 1, wherein each genotyping primer is selected so that the masses of the extended products and primers do not overlap.

12. The method of claim 1, further comprising a free $Mg^{2+}$ concentration between 1.0-2.0 mM.

13. The method of claim 1, further comprises inactivating one or more amplification reactants.

14. The method of claim 13, wherein the one or more amplification reactants includes a nucleotide.

15. The method of claim 14, wherein the nucleotide is inactivated by a phosphatase.

16. The method of claim 13, wherein the one or more amplification reactants includes a primer.

17. The method of claim 16, wherein a primer is inactivated by a nuclease.

18. The method of claim 17, wherein the nuclease is an exonuclease.

19. The method of claim 1, wherein for each amplification primer pair, one primer is in lower concentration than the other primer.

20. The method of claim 1, wherein the lower concentration primer for a particular nucleic acid-target is in the same orientation as the genotyping primer for that nucleic acid-target region.

21. The method of claim 1, wherein the amplified products of the amplifying step are single-stranded nucleic acid molecules.

* * * * *